US008338624B2

(12) United States Patent
Kohen et al.

(10) Patent No.: US 8,338,624 B2
(45) Date of Patent: Dec. 25, 2012

(54) ISOFLAVONE DERIVATIVES AND USES THEREOF

(75) Inventors: Fortune Kohen, Tel Aviv (IL); Dalia Somjen, Rehovot (IL); Naftali Stern, Nir Zvi (IL); Veronica Frydman, Rehovot (IL); Tikva Kulik, Rehovot (IL); Batya Gayer, Rehovot (IL)

(73) Assignees: Yeda Research and Development Co., Ltd., Rehovot (IL); Medical Research and Infrastructure Fund of Tel-Aviv Sourasky Medical Center, Tel Aviv (IL)

( * ) Notice: Subject to any disclaimer, the term of this patent is extended or adjusted under 35 U.S.C. 154(b) by 475 days.

(21) Appl. No.: 12/527,982

(22) PCT Filed: Feb. 20, 2008

(86) PCT No.: PCT/IL2008/000219
§ 371 (c)(1),
(2), (4) Date: Nov. 20, 2009

(87) PCT Pub. No.: WO2008/102350
PCT Pub. Date: Aug. 28, 2008

(65) Prior Publication Data
US 2010/0069478 A1 Mar. 18, 2010

Related U.S. Application Data

(60) Provisional application No. 60/902,062, filed on Feb. 20, 2007, provisional application No. 60/983,276, filed on Oct. 29, 2007.

(51) Int. Cl.
*C07D 311/30* (2006.01)
*C07H 15/26* (2006.01)
*A61K 31/7048* (2006.01)
*A61K 31/352* (2006.01)

(52) U.S. Cl. ............... 549/403; 536/8; 514/27; 514/456

(58) Field of Classification Search .................. 549/403; 514/456, 27; 536/8
See application file for complete search history.

(56) References Cited

FOREIGN PATENT DOCUMENTS
WO 03079965 A2 10/2003

OTHER PUBLICATIONS

Gamble et al., "Phenoxodiol, An Experimental Anticancer Drug, Shows Potent Antiangiogenic Properties in Addition to Its Antitumour Effects," Int. J. Cancer: 118, 2006, pp. 2412-2420.
Kamsteeg et al., "Phenoxodiol-An Isoflavone Analog-Induces Apoptosis in Chemoresistant Ovarian Cancer Cells," Oncogene, 2003, pp. 2611-2620.
Kohen et al., "Synthesis and Evaluation of the Antiproliferative Activities of Derivatives of Carboxyalkyl Isoflavones Linked to N-T-Boc-Hexylenediamine," J. Med. Chem., 2007, pp. A-F, vol. xxx, No. xx.
Somjen et al.,"6-Carboxymethyl Genistein: A Novel Selective Oestrogen Receptor Modulator (SERM) With Unique, Differential Effects on the Vasculature, Bone and Uterus," Journal of Endocrinology, 2002, pp. 415-427, vol. 173, Society of Endocrinology, Great Britain.
Uckun et al., "Cytotoxic Activity of Epidermal Growth Factor-Genistein Against Breast Cancer Cells," Clinical Cancer Research, 1998, pp. 901-912, vol. 4.

*Primary Examiner* — Bernard Dentz
(74) *Attorney, Agent, or Firm* — Browdy and Neimark, PLLC

(57) ABSTRACT

Isoflavone derivatives are provided comprising a carboxyalkylene moiety linked via its alkylene chain to the aromatic ring and via its carboxy group to an aminoalkyleneamino residue, which, in turn, is covalently linked to a functional group B. The isoflavone derivatives are preferably derived from biochanin A, genistein, and daidzein, and the functional group B is preferably an amino protecting group. These isoflavone derivatives are useful for treating or preventing diseases or disorders associated with estrogen receptor functioning.

19 Claims, 7 Drawing Sheets

Days of tumor measurements

Tumor measurements (Days)

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
aattctgaca atcgacgcca g                                          21

<210> SEQ ID NO 2
<211> LENGTH: 23
<212> TYPE: DNA

```
<213> ORGANISM: Artificial Sequence
<220> FEATURE:
<223> OTHER INFORMATION: Synthetic

<400> SEQUENCE: 2
gtgcttcaac attctccctc ctc                                         23

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tgctttggtt tgggtgattg c                                           21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
tttgctttta ctgtcctctg c                                           21
```

ISOFLAVONE DERIVATIVES AND USES THEREOF

FIELD OF THE INVENTION

The present invention relates to isoflavone derivatives and, more particularly, to certain isoflavone derivatives which are active as estrogen receptor modulators, and to their uses.

BACKGROUND OF THE INVENTION

Estrogens, a family of related molecules that stimulate the development and maintenance of female characteristics and sexual reproduction, act on target tissues by binding to estrogen receptors. Some drugs that block the action of estrogen in certain tissues actually can mimic the action of estrogen in other tissues. Such selectivity is made possible by the fact that the estrogen receptors (ERs) of different target tissues vary in chemical structure. There are two ERs: the ERα is found in the endometrium, breast cancer cells and ovarian stroma cells, while the ERβ is found in kidney, brain, bone, heart, lungs, intestinal mucosa, prostate, and endothelial cells. Some estrogenic or estrogen-like compounds may have different binding affinities for ERα and ERβ. These differences allow estrogen-like drugs to interact in different ways with the estrogen receptors of different tissues, namely, they can selectively activate (or block) one type of ER or to promote ER interactions with different proteins such as transcriptional co-activator or co-repressor proteins. Such drugs are called selective estrogen receptor modulators, or SERMs, because they selectively stimulate or inhibit the estrogen receptors of different target tissues.

Isoflavones are a class of phytoestrogen plant-derived compounds, which exhibit multiple biological effects and, in some systems, operate through estrogen receptors, upon which they may act as agonists, antagonists or mixed agonist-antagonists. Soybeans and soy products and red clover are the richest sources of isoflavones in the human diet.

Isoflavones and certain derivatives thereof are known to compete with estrogen on binding to estrogen receptors (ERs), and can thus be used for modulation of ERs functioning. Having the capability to modulate ER activity, isoflavone and derivatives thereof may be useful to treat or prevent a variety of diseases and conditions related to estrogen receptor functioning in mammals, preferably humans. Epidemiological and in vitro and in vivo animal studies indicate that isoflavones are promising agents for cancer chemoprevention and as inhibitors of tumor progression.

The isoflavones that have been most studied are genistein, biochanin A and daidzein. These compounds may act as weak estrogens or as anti-estrogens, depending on the cell type and concentration of isoflavone used. In various estrogen sensitive human cancer cell lines (e.g breast, colon, etc) these isoflavones can act as weak estrogens and stimulate cell growth at concentrations ranging from 0.1 to 20 µM, while inhibiting cell proliferation at concentrations greater than 20 µM. The affinity of most isoflavones to the two subtypes of ER is low (Kuiper et al. 1998), with the exception of genistein, which shows a stronger selectivity for ERβ over ERα. Both genistein and daidzein display 100-fold greater sensitivity (Harris et al., 2005) for activating transcription in transfected cells via ERβ compared to ERα.

The mechanisms underlying the anti-proliferative effects of these compounds vary significantly among the various isoflavones and the type of cell under investigation. For example, inhibition of cell proliferation by isoflavones may involve interference with signaling via the epidermal growth factor receptor kinase (Akiyama et al., 1987), effects on cell cycle (Agarwal 2000), caspases or transforming growth factor β signaling (Kim et al., 1998). Several approaches have been applied in an attempt to utilize and improve the cytotoxic potency of isoflavones. These include targeting of the EGF receptor in breast cancer cells by using a conjugate of genistein coupled to EGF, EGF-Gen (Uckun et al., 1998); generation of synthetic derivatives of chromen-4-one (the minimal structural motif of genistein) complexed to copper (Barve et al., 2006); and reducing the ketone group at position C-4 of daidzein, to yield the dihydro derivative of daidzein phenoxodiol. In in vitro studies, EGF-Gen and the synthetic derivatives of the structurally modified genistein analogue, chromen-4-one complexed to copper, exerted higher cytotoxic activity than genistein, with lower $IC_{50}$ in breast cancer (Uckun et al., 1998) and pancreatic cancer cells (Sarkar et al., 2006). Phenoxodiol showed strong apoptotic (Kamsteeg et al., 2003) and anti-angiogenic activities (Gamble et al., 2006) in ovarian carcinoma in vitro and reduced tumor volume of ovarian xenografts in vivo (Mor et al., 2006).

Previous studies of the present inventors have shown that a derivative of genistein, 6-carboxymethylene genistein, behaved like a selective estrogen receptor modulator, with unique and differential effects on the vasculature, bone, and uterus (Somjen et al., 2002).

WO 03/079965, of the same applicants, discloses carboxy derivatives of isoflavones such as biochanin A, formononetin, daidzein and genistein, and conjugates thereof with a bioactive moiety, particularly daunomycin. These isoflavone derivatives are said to exhibit selective estrogen receptor modulation, i.e., to display both weak estrogenic and anti-estrogenic properties in various cancer cell lines.

In order to more effectively inhibit cell growth, it is still desirable to develop derivatives of isoflavones exhibiting more potent inhibitory activity than the parent isoflavones, but with only minimal estrogenic activity.

SUMMARY OF THE INVENTION

The present invention relates to novel isoflavone derivatives of the formula I herein, which comprise a carboxyalkylene moiety linked via its alkylene chain to the aromatic ring and via its carboxy group to an aminoalkyleneamino residue, which, in turn, is covalently linked to a functional group B. This functional group is preferably an amino protecting group, more preferably tert-butoxycarbonyl. In these isoflavone derivatives, the N-protecting moiety provides a metabolic stability to the molecule and the long aminoalkyleneamino chain causes a steric hindrance, thus conferring a potential antagonistic activity to the molecule when and if it binds to an estrogen receptor.

In one preferred embodiment, the novel isoflavone derivatives are of the formula Ia herein, and are derived from biochanin A or genistein. In most preferred embodiments, the isoflavone derivatives of the formula Ia are the compound herein designated 7 and 8.

In another preferred embodiment, the isoflavone derivatives are of the formula Ib herein, and are derived from daidzein, most preferably the compound herein designated compound 9.

The present invention further provides pharmaceutical compositions comprising isoflavone derivatives of the formula I, more preferably derivatives of the formula Ia or Ib, most preferably compounds 7, 8, or 9. The pharmaceutical compositions of the invention are useful for treating or preventing a disease associated with estrogen receptor functioning.

In another aspect, the present invention provides a method of treating or preventing a disease or disorder associated with estrogen receptor functioning, comprising administering to a subject in need thereof a therapeutically effective amount of a compound of formula I.

In one preferred embodiment, the method of the invention is useful for the treatment of cancer, more preferably breast cancer, uterus cancer, ovarian cancer, colon cancer, gastric cancer, adrenal cancer and prostate cancer.

Further provided by the invention is the use of an isoflavone derivative of formula I, for the preparation of a pharmaceutical composition for the treatment or prevention of a disease associated with estrogen receptor functioning.

BRIEF DESCRIPTION OF THE FIGURES

FIGS. 1A, 1B display the results obtained for genistein and its derivatives, and FIGS. 1A, 1C display the results obtained for biochanin A and its derivatives. BA=compound 1; cBA=compound 4; t-BoccBA=compound 7; G=compound 2; cG=compound 5; t-BoccG=compound 8.

DETAILED DESCRIPTION OF THE INVENTION

Figure 1A:
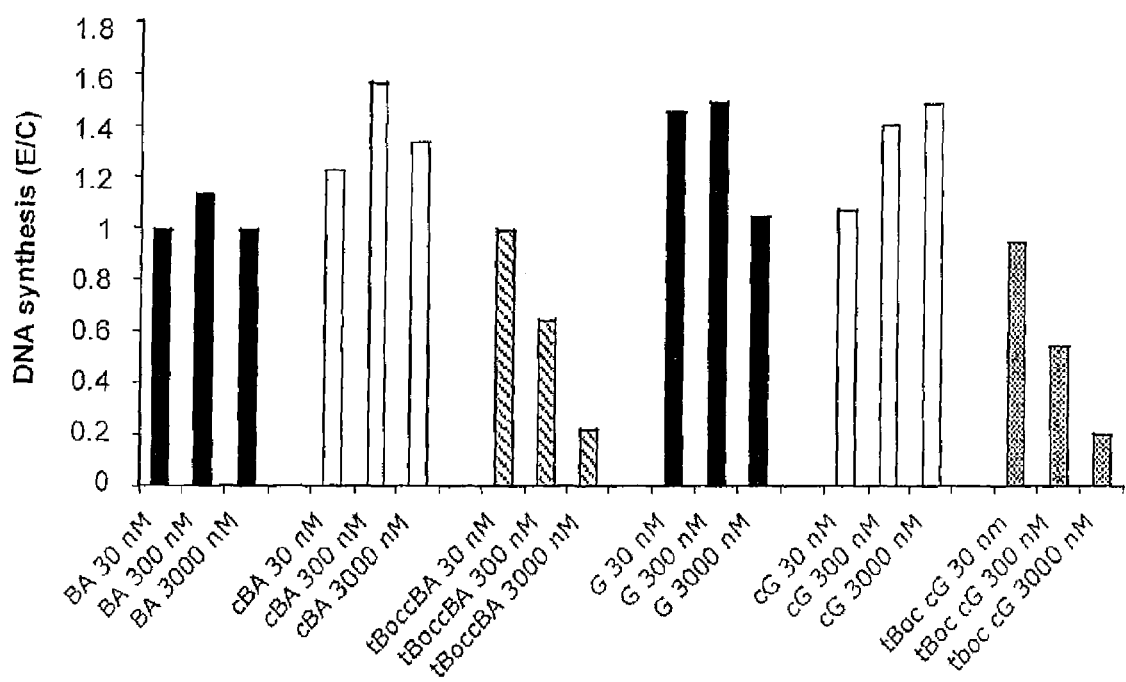
FIGS. 1A-1C are graphs showing the effect of isoflavone derivatives on DNA synthesis in human 320DM colon cancer cells assessed by [$^3$H]-thymidine incorporation. Results, calculated as means±SD of 8-16 incubates from 2-4 experiments, are expressed as the ratio between [$^3$H]-thymidine incorporation in isoflavone treated versus control cells (E/C).

It has been previously found by the present inventors that certain carboxyalkylene derivatives of isoflavones (genistein, biochanin A and daidzein), behaved like selective estrogen receptor modulators, showing unique and differential effects, e.g., on the vasculature, bone, and uterus.

The present invention provides novel isoflavone derivatives that exhibit more potent inhibitory activity on cancer cell growth than the parent isoflavones and their carboxyalkylene derivatives, while retaining no estrogenic activity.

The novel isoflavone derivatives provided by the present invention have been designed such that a carboxyalkylene chain linked at position 2, 5, 6, 7 and/or 8, preferably at position 2 and/or 7, of the isoflavone molecule, is lengthened by covalent linkage to an amino alkyleneaminochain wherein the terminal amino group is protected with an amino protecting group. In this format, the N-protecting moiety serves as a metabolically stable group, and the long aminoalkyleneamino chain on the isoflavone molecule may provide steric hindrance when and if the molecule is bound to a membranal or nuclear estrogen receptor. This approach was applied in the preparation of tert-butoxycarbonyl (t-Boc) derivatives of carboxyalkylene genistein, carboxyalkylene biochanin A and 7-(O)-carboxyalkylene daidzein. The t-Boc derivatives of the carboxyalkylene isoflavones showed no estrogenic activity. Moreover, unlike the parent isoflavones or the carboxyalkylene isoflavones, these t-Boc derivatives inhibited DNA synthesis in vitro in a dose dependent manner at concentrations ranging from 15 to 3000 nmol/l in a number of cancer cell types such as ovarian, colon, adrenal and prostatic cell lines expressing mRNAs for estrogen receptors (ER) α and β, in which ERβ was more abundant than ERα, but had little effect in normal cells, e.g., vascular smooth muscle cells (VSMC). When tested in vivo, these t-Boc derivatives of the carboxyalkylene isoflavone were capable of reducing tumor volume by >50% in mice implanted with ovarian xenografts, and did not cause death or weight loss in tumor bearing mice.

The chemical structures of biochanin A (compound 1), genistein (compound 2), daidzein (compound 3), and their carboxyalkylene derivatives (compounds 4, 5, 6, respectively), are depicted in Scheme 1, just before the references.

Thus, in one aspect, the present invention provides isoflavone derivatives of the general formula I:

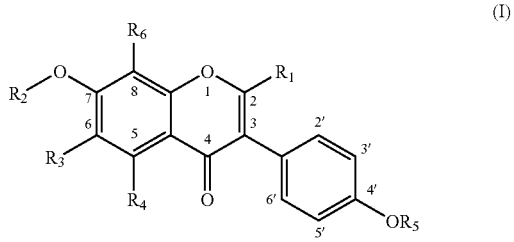
(I)

wherein $R_1$ is H or $R_7$—CON($R_8$)—$R_9$—N($R_8$)—B;

$R_2$ is H, ($C_1$-$C_6$) alkyl, $R_9$—COO$R_{10}$, glucosyl, or $R_7$—CON($R_8$)—$R_9$—N($R_8$)—B;

$R_3$ is H or $R_7$—COO$R_{10}$;

$R_4$ is H, OH, —O$R_9$—CO$R_{10}$ or $R_7$—COO$R_{10}$;

$R_5$ is H, ($C_1$-$C_6$) alkyl or $R_7$—COO$R_{10}$ $R_6$ is H or $R_7$—COO$R_{10}$;

$R_7$ is ($C_1$-$C_{20}$) alkylene, —O—($C_1$-$C_{20}$) alkylene or ($C_2$-$C_{20}$) alkenylene;

$R_8$ is H or ($C_1$-$C_3$) alkyl;

$R_9$ is ($C_1$-$C_{20}$) alkylene or ($C_2$-$C_{20}$) alkenylene;

$R_{10}$ is H or $R_7$—CON($R_8$)—$R_9$—N($R_8$)—B;

B is an amino-protecting group;

provided that at least one of $R_1$ and $R_2$ is $R_7$—CON($R_8$)—$R_9$—N($R_8$)—B;

and pharmaceutically acceptable salts or hydrates thereof.

The terms "amino-protecting group" and "N-protecting group" are used herein interchangeably and mean a functional group covalently linked to a free amino group in order to prevent its participation in chemical reactions due to its basic and nucleophilic nature. Non-limiting examples of N-protecting group suitable for the purpose of the invention are tert-butoxycarbonyl (t-Boc); benzyloxycarbonyl (Z); 4-methoxybenzyloxycarbonyl (Z(OMe)); 2-nitrobenzyloxycarbonyl (Z($NO_2$)); 2-(biphenyl-4-yl)-2-propoxycarbonyl (Bpoc); and fluorenyl-9-methoxycarbonyl (Fmoc). In more preferred embodiments, the amino protecting group is t-Boc.

The term "alkyl", as used herein, refers to a linear or branched alkyl radical having up to 20 carbon atoms (a ($C_1$-$C_{20}$) alkyl). Preferably, the alkyl is a lower alkyl of up to 6 carbon atoms i.e., a ($C_1$-$C_6$) alkyl more preferably a ($C_1$-$C_3$) alkyl. Examples of lower alkyls include methyl, ethyl, n-propyl, isopropyl, n-butyl, t-butyl, pentyl and hexyl. Examples of higher alkyl having 7 to 20 carbon atoms include heptyl, octyl, decyl, octadecyl and the like.

The term "($C_1$-$C_{20}$) alkylene" refers to a linear divalent hydrocarbon chain of the formula —$C_nH_{2n}$—, having 1 to 20 carbon atoms. Examples of linear alkylene chains include methylene, ethylene, propylene, butylene, pentylene, hexylene, octylene and the like. In preferred embodiments, the alkylene is a lower alkylene of 1 to 6 carbon atoms, most preferably methylene or hexylene.

The term "($C_2$-$C_{20}$) alkenylene", as used herein, refers to a linear divalent hydrocarbon chain having 2 to 20 carbon atoms and one or more double bonds, and includes, for example, vinylene, propenylene, butenylene, pentenylene, hexenylene, or $C_{16}H_{30}$.

The term "—O—($C_1$-$C_{20}$) alkylene" denotes an oxygen-containing alkylene of 1 to 20 carbon atoms, wherein alkylene is as defined above. Non-limiting example are —OCH$_2$—, OCH$_2$—CH$_2$—, —O—CH$_2$—CH$_2$—CH$_2$—CH$_2$—, —OC$_{15}$H$_{30}$, —OC$_{16}$H$_{32}$, —OC$_{17}$H$_{34}$, —OC$_{18}$H$_{36}$, and the like.

Encompassed within the scope of formula I above are derivatives of isoflavone glycosides, i.e. isoflavone derivatives bound at position 2 to a sugar moiety, preferably glucose. Isoflavones are naturally present in plants, for example in soybeans, as glycosides.

In one preferred embodiment, the present invention provides an isoflavone derivative of the formula Ia:

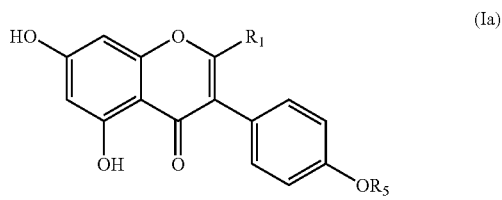

(Ia)

wherein $R_1$ is $R_7$—CON($R_8$)—$R_9$—N($R_8$)—B;

$R_5$ is H or ($C_1$-$C_6$) alkyl;

$R_7$ is ($C_1$-$C_{20}$) alkylene, —O—($C_1$-$C_{20}$) alkylene or ($C_2$-$C_{20}$) alkenylene;

$R_8$ is H or ($C_1$-$C_3$) alkyl;

$R_9$ is ($C_1$-$C_{20}$) alkylene or ($C_2$-$C_{20}$) alkenylene;

B is an amino-protecting group;

and a pharmaceutically acceptable salt or hydrate thereof.

In a more preferred embodiment, in the compound of formula Ia, $R_5$ is H or ($C_1$-$C_3$) alkyl, $R_7$ is ($C_3$-$C_6$) alkylene, $R_8$ is H or ($C_1$-$C_3$) alkyl and $R_9$ is ($C_3$-$C_8$) alkylene, and B is t-Boc.

In a most preferred embodiment, the compound of formula Ia is herein identified as compound 7 of the formula:

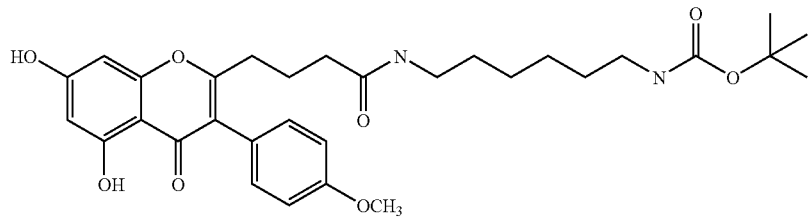

In another most preferred embodiment, the compound of formula Ia is herein identified as compound 8 of the formula:

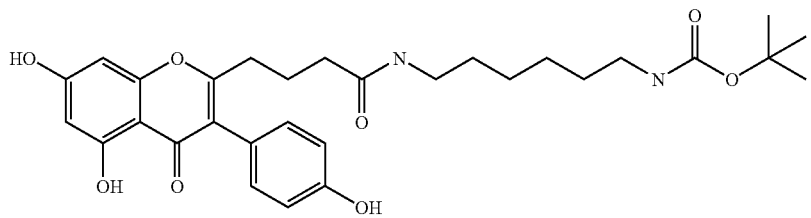

In another preferred embodiment, the compound provided by the invention is an isoflavone derivative of the formula Ib:

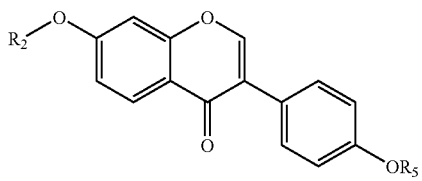

wherein $R_2$ is $R_7$—CON($R_8$)—$R_9$—N($R_8$)—B, and $R_5$, $R_7$, $R_8$, $R_9$, and B are as defined above for formula Ia.

In a more preferred embodiment, $R_5$ in formula Ib is H, $R_7$ is ($C_1$-$C_6$) alkylene, $R_8$ is H or ($C_1$-$C_3$) alkyl, $R_9$ is ($C_3$-$C_{10}$) alkylene and B is t-Boc.

In a most preferred embodiment, the compound of formula Ib is herein identified as compound 9 of the formula:

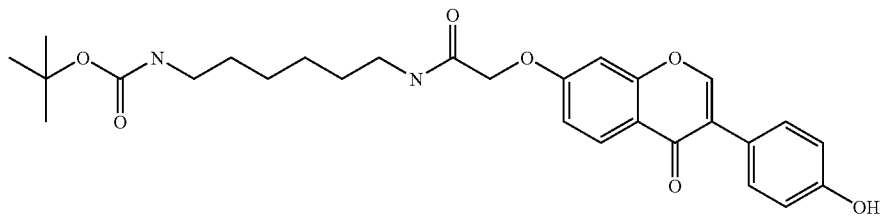

Results of in vitro studies with the compounds 9, 7 and 8 of the present invention, indicate that these compounds exhibit significant (50 to 90%) anti-proliferative effects in a variety of estrogen-sensitive cancer cell lines (gastric, colon, adrenal, ovarian, prostate), at concentrations ranging from 30 nM to 3000 nM. In vitro screening of compound 9 was performed in 60 cell lines (using the National Cancer Institute's (NCI, USA) services). The colon, leukemia, breast cancer, melanoma, ovarian and the non small lung cancer cell lines showed to be more sensitive to the cytotoxic effect of 9.

It is noteworthy that the anti-proliferative effect of the compounds of the invention was more pronounced in cancer cells which preferentially express mRNA for ERβ relative to ERα. In addition, these compounds did not exhibit estrogenic activity and showed moderate (20 to 35%) anti-proliferative effects in T47D breast cancer cell lines expressing more mRNA for ERα than ERβ, and in normal cells (vascular smooth muscle cells) at concentration ranging from 3 μM to 10 μM.

In ovarian and colon cancer cell lines, the anti-proliferative effects of compound 9 is apparently mediated via both ER-dependent and ER-independent mechanisms. In these cell lines, compound 9 showed anti-estrogenic effects, and the anti-mitotic effect of 9 is operative, at least in part through induction of apoptosis.

The results of the above mentioned in vitro studies indicate that the compounds of the invention, acting through estrogen receptors and/or via other mechanisms, may be useful in the treatment of various conditions associated with estrogen receptor functioning.

Thus, in another aspect, the present invention provides a pharmaceutical composition comprising a compound of the formula I as defined above and a pharmaceutically acceptable carrier. In more preferred embodiments, the pharmaceutical composition of the invention comprises a compound of the formula Ia or Ib defined herein. Most preferably the pharmaceutical composition of the invention comprises the compound 7, 8, or 9.

In a further aspect, the present invention provides a method of modulating estrogen receptor functioning, comprising administering to a subject in need thereof a therapeutically effective amount of a compound of formula I herein. Preferably, the compound employed is an isoflavone derivative of the formula Ia or Ib, more preferably, the isoflavone derivative 7, 8 or 9.

The pharmaceutical compositions of the invention, herein sometimes referred to as "formulations", may be administered orally or parenterally, including the intravenous, intramuscular, intraperitoneal, subcutaneous routes, or by rectal or topical application.

In one preferred embodiment, the pharmaceutical composition of the invention is administered orally as an immediate release or modified release dosage form.

The final dosage form may be any of the many variations known in the art. These include, but are not limited to, tablets, pills, hard capsules, soft capsules, and aqueous solutions or suspensions.

The formulations of the invention may further contain water insoluble permeable polymers, herein defined as "modified release polymers", to adjust their release profile. These polymers may either be coated onto formulations such as tablets, microgranules, capsules or pills, or be mixed together with the other ingredients of any of the formulations listed above.

In one embodiment, the pharmaceutical composition is in the form of tablets prepared by mixing the active agent with excipients. Typical excipients include diluents, fillers, binders, lubricants, disintegrants, glidants, colorants, pigments, taste masking agents, modified release polymers, sweeteners, plasticizers, and any acceptable auxiliary substances such as absorption enhancers, penetration enhancers, surfactants, co-surfactants, and specialized oils. Examples of excipients include calcium phosphates, such as dibasic calcium phosphate, anhydrous dibasic calcium phosphate, tribasic calcium phosphate, etc.; microcrystalline cellulose, powdered cellulose; starch, pre-gelatinized starch; sodium starch glycolate; dextrates; mannitol, sorbitol; povidone; ethyl cellulose; lactose; kaolin; silicic acid; lubricants such as magnesium stearate, calcium stearate, stearic acid, mineral oil, glycerin, sodium lauryl sulfate, polyethylene glycol; and/or talc. Sodium starch glycolate, talc and the lubricant magnesium stearate are preferably used for tablet manufacture.

In another embodiment, the tablets of the invention are prepared as modified release tablets and comprise the active agent and the excipients mannitol, microcrystalline cellulose, ethyl cellulose, povidone, sodium starch glycolate and talc. In a more preferred embodiment, the modified release tablets contain the modified release polymer ethyl cellulose mixed together with the other excipients.

In one embodiment, the tablets of the invention are prepared by mixing the active agents with microcrystalline cellulose, lactose or mannitol in the powder form followed by the addition of a solution of polyethylene glycol or a solution of ethyl cellulose, povidone and cyanocobalamin to form a granulated mixture. This granulate is then dried and mixed with sodium starch glycolate and magnesium stearate or talc and prepared as tablets using a rotary punch manufacturing process. Materials and preparation techniques for tablet manufacture useful in the invention can be found in e.g., Remington Pharmaceutical Sciences, 21$^{st}$ Edition, 2005, Lippincott Williams and Wilkins eds.

In another preferred embodiment, the tablets of the invention are formed by mixing all the ingredients in solid state and then directly compressing them into a tablet form, i.e., a so-called direct compression technique.

The palatability of the tablets can be improved by coating the tablets with a taste-masking agent such as a methyacrylic acid copolymer (e.g. Eudragit), methylcellulose or methylhydroxypropyl cellulose.

In another embodiment, the pharmaceutical composition is in the form of capsules, preferably prepared by mixing the active agent with excipients such as lactose and microcrystalline cellulose, adding a solution of e.g. polyethylene glycol to form a granulated mixture, which is then dried. An excipient, preferably talc, is added to the granulate and the mixture is then filled into capsules.

In another preferred embodiment, the present invention provides an aqueous solution or dispersion comprising the isoflavone derivative as the active agent. When aqueous suspensions are required for oral use, the active ingredient is combined with emulsifying and suspending agents. If desirable, certain sweetening or flavoring agents may be added such as an artificial sweetener, preferably sucralose, microcrystalline cellulose and a powder-based flavoring agent.

In a further embodiment, the formulation of the invention is in the form of a syrup for reconstitution. Any combination of excipients known in the art is suitable for use according to the invention for the preparation of syrup for reconstitution. The excipients may be any of the excipients mentioned above suitable for the preparation of a liquid composition such as sweeteners, taste-masking agents, colorants, diluents etc.

In other preferred embodiments, the pharmaceutical composition of the invention is injected to a subject intravenously, intramuscularly, intraperitonealy or subcutaneously. For these uses, sterile solutions of the active ingredient are usually prepared and the pH of the solutions is suitably adjusted and buffered. For intravenous use, the total concentration of solutes should be controlled in order to render the preparation isotonic.

Due to their interaction with ERs and/or activity through other mechanisms, either related or unrelated to this interaction, the isoflavone derivatives of the present invention may be useful to treat or prevent a variety of diseases and conditions related to estrogen receptor functioning in mammals, preferably humans.

Thus, in another aspect, the present invention provides a method of treating or preventing a disease or disorder associated with estrogen receptor functioning. In a preferred embodiment, the method comprises administering to a subject in need an isoflavone derivative of the formula I herein, more preferably, the compound administered is an isoflavone derivative of the formula Ia or Ib, most preferably, the compound 7, 8 or 9.

The variety of diseases and conditions related to estrogen receptor functioning include, but is not limited to, bone loss, bone fractures, osteoporosis, metastatic bone disease, Paget's disease, periodontal disease, cartilage degeneration, endometriosis, uterine fibroid disease, hot flashes, cardiovascular diseases, impairment of cognitive functioning, age-related mild cognitive impairment, cerebral degenerative disorders, restenosis, gynecomastia, vascular smooth muscle cell proliferation, obesity, incontinence, anxiety, depression particularly perimenopausal depression, post-partum depression and manic depression, premenstrual syndrome, dementia, obsessive compulsive behavior, attention deficit disorder, sleep disorders, irritability, impulsivity, multiple sclerosis, Parkinson's disease, inflammation, inflammatory bowel disease, irritable bowel syndrome, sexual dysfunction, hypertension, retinal degeneration and cancer, in particular of the breast, ovary, uterus, colon, stomach, kidney and prostate.

Ovarian cancer is often discovered in advanced stages, resulting in a 20% five-year survival rate. Although chemotherapeutic agents are widely used for the treatment of ovarian cancer, chemoresistance remains a major problem. Interestingly, phenoxodiol, a derivative of daidzein, shows promising results in the treatment of ovarian cancer (Kamsteeg et al., 2003). Therefore, the compounds of the present invention may offer a novel approach to the treatment of ovarian cancer.

No effective treatment presently exists for human adrenal cancer. The efficacy of the t-Boc isoflavone derivatives of the invention, particularly of compound 9 as shown in the in vitro examples herein, holds promise for its potential use in vivo.

Colorectal cancer is one of the most common cancers, often showing poor or partial response to available chemotherapeutic agents. The t-Boc isoflavone derivatives of the present invention inhibit the growth of colon cancer cells in vitro as well as in vivo in a human tumor animal model. Accordingly, these compounds may also be effective in inhibiting colon cancer progression in vivo.

As shown herein, when tested in vivo, the t-Boc isoflavone derivatives of the invention were capable of reducing tumor volume by >50% in mice implanted with ovarian or colon xenografts. It is to be noted that although this effect was comparable in magnitude to the in vivo tumoricidal effect of the known anticancer drug daunomycin, treatment with the t-Boc daidzein derivative of the invention did not cause death or weight loss in tumor bearing mice, unlike the treatment with daunomycin.

Thus, the present invention provides a method for the treatment or prevention of cancer, especially breast cancer, uterus cancer, ovarian cancer, colon cancer, gastric cancer, adrenal cancer and prostate cancer. In a most preferred embodiment, the method of the invention is useful in the treatment of estrogen dependent breast cancer.

Estrogen appears to have an effect on the biosynthesis of cholesterol and other beneficial effects on cardiovascular health. It is believed that estrogen plays a beneficial role in preventing cardiovascular diseases. The mechanism is not well understood, but there are several indications that estrogen can upregulate the low-density lipid (LDL) cholesterol receptors in the liver to remove excess cholesterol. Thus, the isoflavone derivatives of the invention may be employed in a method for treating or preventing a cardiovascular disease or restenosis.

In another embodiment, the method of the invention is employed in the treatment or prevention of impairment of a cognitive function, age-related mild cognitive impairment or cerebral degenerative disorders in a mammal. In the art, estrogen has been shown to have beneficial effects on cognitive functioning, such as relieving anxiety and depression and treating or preventing Alzheimer's disease. Estrogen affects the central nervous system by increasing cholinergic functioning, neurotrophin and neurotrophin receptor expression. Estrogen also increases glutamergic synaptic transmission, alters amyloid precursor processing and provides neuroprotection. Thus, the isoflavone derivatives of the invention acting as ER modulators, may be beneficial for improving cognitive functioning or treating age-related mild cognitive impairment, attention deficit disorder, sleep disorders, irritability, impulsivity, anger management, multiple sclerosis and Parkinson's disease.

The contribution of estrogen receptors in the modulation of emotional processes, such as anxiety has been described in the art. Thus, in another embodiment, the method of the invention is employed in the treatment or prevention of anxiety in a mammal, preferably humans.

In another embodiment, the method of the invention is useful for treating or preventing inflammation, inflammatory bowel disease or irritable bowel syndrome. Inflammatory bowel diseases, including Crohn's disease and ulcerative colitis, are chronic disorders in which the small intensine (bowel) becomes inflamed, often causing recurring abdominal cramps and diarrhea.

In a further embodiment of the method of the invention, the isoflavone derivatives are used for treatment or prevention of sexual dysfunction in males or females.

The compound of the invention may be administered to mammals, preferably humans, either alone or, preferably, in combination with pharmaceutically acceptable carriers or diluents, optionally with known adjuvants, such as alum, in a pharmaceutical composition according to standard pharmaceutical practice. The compound can be administered orally or parenterally, including the intravenous, intramuscular, intraperitoneal, subcutaneous, rectal and topical routes of administration as described above.

In a further aspect, the present invention provides the use of an isoflavone derivative of the formula I, preferably isoflavone derivative of the formula Ia or Ib, more preferably the compound 7, 8 or 9, for the preparation of a pharmaceutical composition for the treatment or prevention of a disease associated with estrogen receptor functioning.

The invention will now be exemplified by the following non-limiting examples.

EXAMPLES

In the Examples and in the figures herein, the derivatives of the invention and the intermediates will be presented by their respective Arabic numbers in bold or by an abbreviation according to the following List of Compounds. The formulas of the compounds appear in Scheme 1 at the end of the description, just before the References.

List of Compounds

1. Biochanin A (BA)
2. Genistein (G)
3. Daidzein (Daid)
4. 2-(3-carboxypropyl)-7,5-dihydroxy-4'-methoxyisoflavone (cBA)
5. 2-(3-Carboxypropyl)-5,7,4'-trihydroxyisoflavone (cG)
6. 7-(O)-Carboxymethyl daidzein (cDaid)
7. 2-[3-carboxy-(6-tert-butoxycarbonylamino)-hexylamino-propyl]-7,5-dihydroxy-4'-methoxyisoflavone (t-Boc-cBA)
8. 2-[3-[N-[6-(tert-Butoxycarbonyl)-aminohexyl]]-caboxamidopropyl]-5,7,4'-trihydroxyisoflavone (t-Boc-cG)
9. 5-{2-[3-(4-Hydroxy-phenyl)-4-oxo-4H-chromen-7-yloxy]-acetylamino}-pentyl)-carbamic acid tert-butyl ester (t-Boc-cDaid)

Materials and Methods
Reagents

All reagents were of analytical grade. N-(tert-butoxycarbonyl)-1,6-hexanediamine hydrochloride, 1,3-dicyclohexylcarbodiimide (DCC), methanol (MeOH), ethanol (EtOH), ethylacetate (EtOAc), trichloroacetic acid (TCA), dimethylformamide (DMF), dichloromethane (DCM), triethylamine (TEA) and estradiol 17β were purchased from Sigma (St-Louis, Mich.); N-hydroxybenzotriazole (HOBt) was purchased from MP Biomedicals (Aurora, Ohio); ICI 182780 was purchased from Tokris (Shirehumpton, Bristol, UK); apoptosis inhibitor Z-VADFMK Me ester was obtained from Axxora (San Diego, Calif.); daunomycin was obtained from Davos Chemical corporation (Upper Saddle, River, N.J.); Methyl-[$^3$H]-thymidine (5 Ci/mmole)) was obtained from New England Nuclear (Boston, Mass.); Neowater was purchased from Do-Coop Technologies, Or-Yehuda.

Cell Culture
Human Cancer Cell Lines

The following estrogen sensitive human cancer cell lines expressing mRNA's for estrogen receptors ERα and β were used: ovarian: MLS and A2780; gastrointestinal tract: N87 and 320DM (colon); adrenal: H295R; prostate: C4-2B; and mammary. T47D.

Gastric (320DM), ovarian A2780 and H295R adrenocarcinoma cancer cells were purchased from ATTC (Rockville, Md.) and were grown according to the instructions of ATTC. Prostatic (C2-4B) and ovarian cancer cells MLS were obtained through the generosity of Prof. M. C. Farach-Carson, University of Delaware, Delaware, and Prof. M. Neeman, Weizmann Institute, Rehovot, Israel respectively. N87 cell were obtained from Prof. Y. Yarden, Weizmann Institute of Science, Rehovot, Israel.

Cells were cultured in MEM supplemented with 10% FCS and antibiotics. Cells were grown to subconfluence and then treated with various hormones or agents as described by Somjen et al. (Somjen et al., 1998). The cells were characterized in terms of expression of mRNAs for estrogen receptors and β by real time PCR, and the results are summarized in Table 1. N87, 320DM and H295R cells expressed mRNAs for both ERs. The ratio of ERα to ERβ was 1:8.5, 1:30 and 1:1.8 in N87, 320DM and H295R cells, respectively. Ovarian A2780 and prostate C4-24 cells expressed mainly mRNA for ERβ, and the ratio of ERβ to ERα was 300:1 and 70:1, respectively. MLS ovarian cells expressed mRNA only for ERβ. The ratio of ERα to ERβ in T47D cells has been reported to be 9:1.

Cells with pronounced ERβ expression were used for screening the biological activity of the various isoflavones and their derivatives.

TABLE 1

Ratio of estrogen receptors α and β in estrogen sensitive normal and cancer cell lines

| Cell line | Ratio ERα/ERβ |
|---|---|
| 320DM (colon) | 1:30 |
| N87 (colon) | 1:8.5 |
| H295R (adrenal) | 1:1.8 |
| A2780 (ovarian) | 1:300 |
| MLS (ovarian) * | |
| C4- 2B (prostatic) | 1:70 |
| VSMC (normal) | 2.7:1 |

* These cells express mRNA only for ERβ

Normal Cells

Human umbilical vascular smooth muscle cells (VSMC) sensitive to estrogen, were grown in culture as described above, and used only at passages 1-3, when expression of smooth muscle actin was clearly demonstrable (Somjen et al. 2000). The ratio of the expression of mRNA for ERα to ERβ was 2.7:1.

Animals

Female CD1 nude mice (8-week old, ~30 g) were housed and handled with free access to food and water in the animal facility according to the guidelines (1996) of the Institutional Animal Care and Use Committee of the Weizmann Institute of Science, Rehovot, Israel.

Methods

Assessment of DNA Synthesis

[$^3$H]-Thymidine incorporation into DNA was used for the assessment of the various effects (proliferative or inhibitory) of various isoflavones, isoflavone derivatives and known cytotoxic drugs in the above-mentioned cells. Cells were grown until subconfluence using conditions described in Somjen et al. (Somjen et al., 1998) and then treated with various agents for 24 or 48 h as indicated. At the end of incubation, [$^3$H]-thymidine was added for two hours. Cells were then treated with 10% ice-cold trichloroacetic (TCA) for 5 min and washed twice with 5% TCA and then with cold ethanol. The cellular layer was dissolved in 0.3 ml of 0.3 M NaOH, aliquots were taken for counting radioactivity, and [$^3$H]-thymidine incorporation into DNA was calculated.

Preparation of Total RNA

Total RNA from cancer and normal cells was extracted using the TRIzol reagent (Gibco Life Technologies) according to the manufacturer's instructions.

Real Time (RT)-PCR

Total RNA (1 μg) was subjected to reverse transcription using the BD Advantage One-Step RT—for PCR kit from BD Biosciences Clontech (Palo Alto, Calif.). For ERα, 5 μl of cDNA was used in the reaction mixture with the primers 5' AATTCTGACAATCGACGCCAG 3' (forward) (SEQ ID NO: 1) and 5' GTGCTTCAACATTCTCCCTCCTC 3' (reverse) (SEQ ID NO: 2), for 30 cycles at 94° C. for 30 seconds, at 57° C. for 30 seconds and at 72° C. for 1 minute. For ERβ, the same amount of cDNA was used with the primers 5' TGCTTTGGTTTGGGTGA TTGC 3' (forward) (SEQ ID NO: 3) and 5' TTTGCTTTTACTGTCCTCTGC 3' (reverse) (SEQ ID NO: 4) for 30 cycles at 94° C. for 30 seconds, at 58° C. for 30 seconds and at 72° C. for 1 minute. Plasmids pRST7ERα and pRST7ERβ (provided by Dr. D. McDonnell, Durham, N.C.) served as positive controls in these reactions.

Statistical Analysis

The significance of differences between the mean values obtained from experimental groups and controls were evaluated by analysis of variance (ANOVA).

In Vitro Cell Line Screening Facilitated by the National Cancer Institute (NCI) of the US An in vitro cell line screen for the t-boc derivative of daidzein (compound 9) was performed at the NCI/NIH US utilizing the In Vitro Cell Line Screening Project (IVCLSP) (National Cancer Institute, Developmental Therapeutics Program, Information Technology Branch, Rockville, Md., USA).

The operation of this screen utilized 60 different human tumor cell lines, representing leukemia, melanoma and cancers of the lung, colon, brain, ovary, breast, prostate, and kidney. The complexity of the 60 cell line dose response produced by the test compound of the invention resulted in a biological response pattern, which was analyzed by pattern recognition algorithms (e.g., the COMPARE program. See: http://dtp.nci.nih.gov/docs/compare/compare.html). Using these algorithms, it is possible to assign a putative mechanism of action to a test compound, or to determine that the response pattern is unique and not similar to that of any of the standard prototype compounds included in the NCI database.

To facilitate analysis of the data, three endpoints were calculated for each cell line: The $GI_{50}$ value, which is the negative $\log_{10}$ of the concentration required to inhibit the growth of that cell line by 50% (relative to untreated cells); TGI, the negative $\log_{10}$ of minimum concentration that causes total growth inhibition; and $LC_{50}$, which reflects the negative $\log_{10}$ concentration needed to kill 50% of the cells. A Mean Graph was used as a way of easily visualizing the results from all 60 cell lines at once. To generate this graph, the mean of $GI_{50}$ values across all 60 cell lines was calculated. For each cell line, the difference between the $GI_{50}$ for that cell line and the mean $GI_{50}$ across all cell lines is calculated. When these differences are graphed, it becomes apparent at a glance which cell lines are more sensitive (those with bars deflecting to the right of the mean), and which cell lines are less sensitive (bars deflecting to the left).

The methodology of the in vitro cancer screen and data analysis are described in details in the website http://dtp.nci.nih.gov/branches/btb/ivclsp.html.

Example 1

Synthesis of Compound 7

The t-Boc isoflavones derivatives were prepared in two steps. In the first step, carboxyalkylene derivatives of the isoflavones were synthesized using established procedures. In the second step, the carboxyalkylene isoflavones were covalently linked to N-(tert-butoxycarbonyl)-1,6-hexylenediamine (i) Synthesis of Compound 4

2-[3-(Ethoxycarbonyl)propyl]-7,5-dihydroxy-4'-methoxyisoflavone (350 mg, 0.88 mmol), prepared according to Pelter et al. (Pelter et al, 1998), was dissolved in a mixture of EtOH (35 ml) and 10% aq. NaOH (35 ml). The solution was stirred at room temperature for 24 h. The organic solvent was then evaporated and H$_2$O (35 ml) was added. The mixture was cooled in an ice-water bath and the pH was adjusted to 4 with conc. HCl. The resulting mixture was left overnight in the refrigerator to complete the precipitation of the product. The solid was collected by filtration, washed with cold water and dried under vacuum. The solid was dissolved in a small amount of EtOAc and evaporated almost completely, leaving a solid and a very small amount of EtOAc, which was removed with a pipette carrying with it some of the impurities. The resulting pinkish solid was dried under vacuum (170 mg, 52%) and identified as compound 4.

$^1$H NMR (250 MHz, acetone-d$_6$) δ 1.98 (m, 2H), 2.33 (t, 2H, J=7.2 Hz), 2.65 (t, 2H, J=7.3 Hz), 6.25 (d, 1H, J=2.1 Hz), 6.43 (d, 1H, J=2.1 Hz), 7.00 (d, 2H, 6.8 Hz), 7.25 (d, 2H, 6.8 Hz).

ESIMS (ES+): m/z 393.53 ([M+Na]$^+$, 80), 371.51 ([M+H]$^+$, 60); (ES−): m/z 369.37 ([M−H]$^-$, 100), 739.69 ([2M−H]$^-$, 25).

(ii) Synthesis of Compound 7

Compound 4 (50 mg, 0.14 mmol) was dissolved under N2 in a mixture of dry dichloromethane (DCM; 1 ml) and dry dimethylformamide (DMF; 0.25 ml). To this mixture, N-hydroxybenzotriazole (HOBt; 26 mg, 0.17 mmol) was added followed by 1,3-dicyclohexylcarbodiimide (DCC; 98 mg, 0.47 mmol), and the mixture was stirred for 30 min. Then, N-(tert-butoxycarbonyl)-1,6-hexanediamine hydrochloride (37 mg, 0.15 mmol) was added followed by triethylamine (TEA; 21 μl, 0.46 mmol). The mixture was flushed with N$_2$, sealed and stirred overnight at room temperature. The solid was filtered off and the filtrate was diluted with Cl$_2$CH$_2$ (DCM; 20 ml), washed with 0.1 N HCl (2×3 ml), H$_2$O (1×3 ml) and brine (2×3 ml). The organic layer was dried over Na$_2$SO$_4$ and evaporated leaving thick yellow oil, which was purified by column chromatography using a gradient of DCM/acetone from 8:1 to 8:2. Compound 7, the t-Boc derivative of carboxy propyl biochanin A, was isolated as a colorless oil (50 mg, 66%).

$^1$H NMR (250 MHz, acetone-d6) d 1.19-1.43 (m, 8H), 1.38 (s, 9H), 2.01 (m, 2H), 2.14 (m, 2H), 2.59 (t, 2H, J=7.5 Hz), 2.85-3.11 (m, 4H) 3.84 (s, 3H), 6.24 (d, 1H, J=2.1 Hz), 6.42 (d, 1H, J=2.1 Hz), 6.99 (d, 2H, J=8.8 Hz), 7.24 (d, 2H, J=8.8 Hz).

Example 2

Synthesis of Compound 8

The t-Boc derivative of genistein, Compound 8, was prepared from the corresponding carboxypropylene derivative of the isoflavone (compound 5) as follows:

(i) Synthesis of Compound 5

To a solution of 2-[3-(ethoxycarbonyl)propyl]-7,5-dihydroxy-4'-methoxyisoflavone (104 mg, 0.26 mmol), prepared according to Pelter et al. (Pelter et al, 1998) in anhydrous DCM (2 ml) at −78° C. under nitrogen, 1.0 M BBr$_3$ in DCM (2.1 ml, 2.1 mmol) was added slowly. The mixture was allowed to warm gradually to room temperature overnight. The mixture was then cooled in an ice bath and anhydrous MeOH (2 ml) was added slowly. The solvents were evaporated under reduced pressure leaving a brown solid that was purified by column chromatography on silica gel (gradient elution: DCM to DCM/acetone 8:2) yielding 2-[3-(methoxycarbonyl)propyl]-5,7,4'-trihydroxyisoflavone as a solid (72 mg, 75%).

$^1$H NMR (acetone-d$_6$) δ 1.99 (quintet, 2H, J=7.3 Hz, H-2"), 2.34 (t, 2H, J=7.3 Hz, H-3"), 2.64 (t, 2H, J=7.3 Hz, H-1"), 3.55 (s, 3H, CO$_2$CH$_3$), 6.24 (d, 1H, J=2 Hz, H-6), 6.41 (d, 1H, J=2 Hz, H-8), 6.90 (d, 2H, J=8.5 Hz, H-3', H-5'), 7.12 (d, 2H, J=8.5 Hz, H-2', H-6').

In the second step of the reaction, 10% aq. NaOH (7 ml) was added to a solution of 2-[3-(methoxycarbonyl)propyl]-5,7,4'-trihydroxyisoflavone (70 mg, 0.189 mmol) in EtOH (7 ml), and the mixture was stirred for 24 h at room temperature. The EtOH was removed under reduced pressure and H$_2$O (7 ml) was added. The solution was acidified to pH 3.5 with 35% HCl and the mixture was left overnight at 4° C. The solid, identified as compound 5, was collected by filtration, washed with cold water and dried under vacuum (53 mg, 79%).

$^1$H NMR (acetone-d$_6$) δ 1.98 (quintet, 2H, J=7.3 Hz, H-2"), 2.34 (t, 2H, J=7.3 Hz, H-3"), 2.65 (t, 2H, J=7.3 Hz, H-1"), 6.24 (d, 1H, J=2.1 Hz, H-6), 6.42 (d, 1H, J=2.1 Hz, H-8), 6.90 (d, 2H, J=8.6 Hz, H-3', H-5'), 7.13 (d, 2H, J=8.6 Hz, H-2', H-6').

(ii) Synthesis of Compound 8

A solution of compound 5 (25 mg, 0.07 mmol) in dry DCM (0.51 ml) and dry DMF (0.13 ml) under Nitrogen was treated with HOBt (13.5 mg, 0.088 mmol) followed by DCC (50.81 mg, 0.25 mmol). The flask was sealed and the mixture was stirred at room temperature for 30 min. N-(tert-butoxycarbonyl)-1,6-hexanediamine hydrochloride (19.2 mg, 0.076 mmol) was added, followed by TEA (11 μl, 0.079 ml). The flask was flushed with nitrogen, sealed and the mixture was stirred overnight. The solid was filtered off and the filtrate was diluted with DCM (20 ml) and washed with 0.1 M HCl (2×1.6 ml), H$_2$O (1.6 ml) and brine (2×1.6 ml), dried over Na$_2$SO$_4$ and evaporated. The residue was purified by column chromatography on silica gel (gradient elution of from 8:1 to 7:3 DCM/acetone), yielding compound 8 as a white foam (30 mg, 77%).

$^1$H NMR (acetone-d$_6$) δ 1.1-1.5 (m, 8H, 4×CH$_2$), 1.40 (s, 9H, t-Bu), 1.99 (m, 2H, H-2"), 2.05 (m, 2H, H-3"), 2.60 (t, 2H, J=7.1, H-1"), 2.95 (m, 4H, 2×CH$_2$—N), 6.23 (d, 1H, J=2.1 Hz, H-6), 6.41 (d, 1H, J=2.1 Hz, H-8), 6.90 (d, 2H, J=8.6 Hz, H-3', H-5'), 7.13 (d, 2H, J=8.6 Hz, H-2', H-6').

MS (ES+): m/z (%)=577 [(M$^+$+Na), 100], 1131 [(2M$^+$+Na), 27]. MS (ES−): m/z (%)=553 [(M$^+$-H), 100], 1108 [(2M$^+$-H), 27].

Example 3

Synthesis of Compound 9

The t-Boc derivative of daidzein, compound 9, was prepared from the corresponding carboxymethylene derivative of the isoflavone (compound 6) as follows:

Compound 6, prepared according to Bennetau-Pelissero et al. (Bennetau-Pelissero et al., 2000) (117 mg, 0.37 mmol) was dissolved in dry DCM (2.8 ml) under N$_2$. Dry DMF (1.2 ml) was added followed by DCC (272 mg, 1.32 mmol) and HOBt (73 mg, 0.48 mmol). The flask was flushed with N$_2$, sealed and stirred at room temperature. After 1 h, t-Boc-1,6-hexanediamine hydrochloride (103 mg, 0.41 mmol) was added followed by triethylamine (0.06 ml, 43.5 mg, 0.43 mmol). The flask was flushed with N$_2$, sealed and stirred overnight at room temperature. The solid was removed by filtration and the filtrate was diluted with Cl$_2$CH$_2$ (55 ml), washed with 0.1 M HCl (2×9 ml), H$_2$O (1×9 ml), brine (2×9 ml) and dried over Na$_2$SO$_4$. The solvents were evaporated under reduced pressure leaving a residue that was purified by column chromatography on silica gel, using a gradient of Cl$_2$CH$_2$/acetone 8:1 to 8:2. Compound 9 was isolated as a colorless oil (90 mg, 48%).

$^1$H NMR (250 MHz, Cl$_3$CD) δ 1.20-1.80 (m, 8H, 4×CH$_2$), 3.10 (m, 2H, —CH$_2$—N), 3.40 (m, 2H, —CH$_2$—N), 4.60 (s, 1H), 6.85 (d, 1H, J=2.1 Hz), 6.90 (AA'BB', 2H), 7.05 (dd, 1H, J=8.3 Hz, J=2.1 Hz), 7.45 (AA'BB', 2H), 7.95 (s, 1H), 8.25 (d, 1H, J=8.3 Hz).

MS (ES+): m/z (%)=533 [(M+Na$^+$), 100], 1044 [(2M+Na$^+$), 35]. MS (ES−): m/z (%)=545 [(M−H)+Cl$^−$ adduct, 100].

Example 4

In Vitro Effect of T-Boc Isoflavones Derivatives and Estradiol on DNA Synthesis in Cells Expressing Predominantly ERβ

The t-Boc derivatives 7, 8 and 9 were first screened for their growth inhibitory activity in estrogen sensitive cancer cell lines (see Table 1) expressing mRNAs for ERα and ERβ in which ERβ expression was more pronounced than ERα, i.e., 320DM colon, MLS and A2780 ovarian, H295R adrenal, C4-2B prostatic cancer cell lines as well as normal VSMC cells, using a concentration of 3 μM (or 0.3 μM for C4-2B prostatic cells). For comparison, the effect of estradiol 17β (E2) was measured in these cells. The results, calculated as mean±SD of 8-16 incubates from 2-4 experiments are presented in Table 2, as the ratio between experimental and control (E/C) DNA synthesis in the tested cells. When all three t-Boc derivatives were compared in this setting, compound 9 had the most potent inhibitory effect on cell growth, as assessed by inhibition of DNA synthesis.

In cancer cells treated with 30 nM estradiol, DNA synthesis was stimulated by 139 to 210%. In normal VSMC, on the other hand, E2 at 30 nM inhibited DNA synthesis (Table 2), but stimulated DNA synthesis in these cells at 3 nM (data not shown).

Figure 1B:
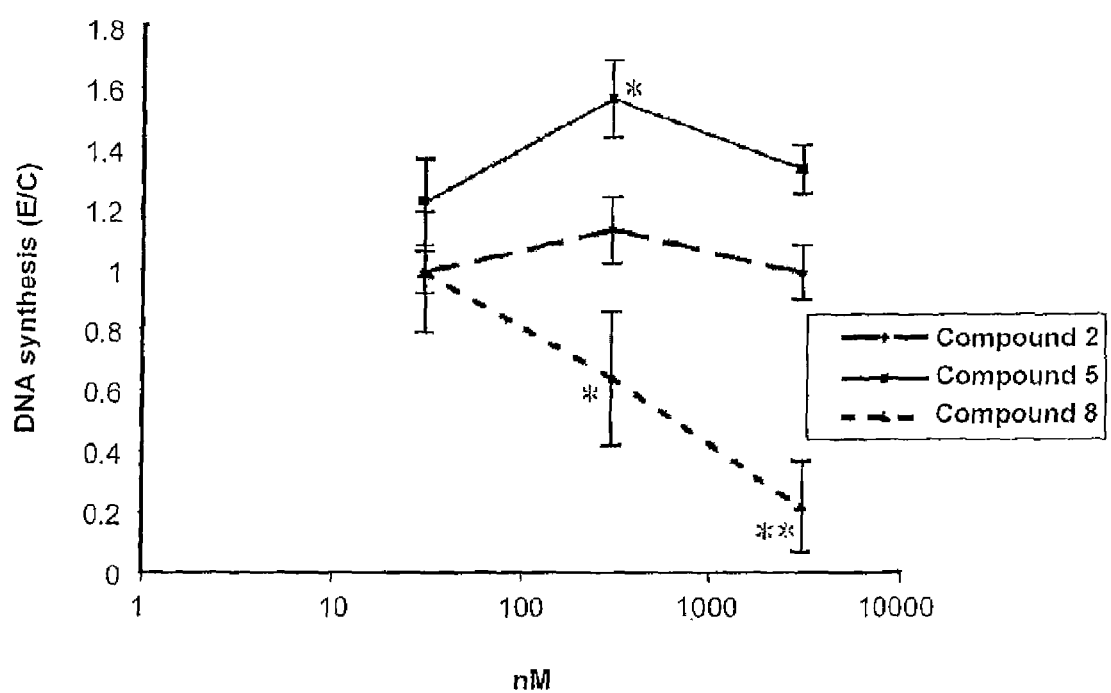

Genistein and its Derivatives (Compounds 2, 5 and 8)
(i) Cancerous Cells of the Gastrointestinal Tract 320DM colon cancer cells. Both compound 2 (30 to 300 nM) and its 2-carboxypropylene derivative 5 (30 to 3000 nM), significantly stimulated [$^3$H]-thymidine incorporation into DNA, as shown in FIGS. 1A and 1B. On the other hand, the t-Boc derivative 8 (30 to 3000 nM), elicited a significant growth inhibitory effect in these cells.

(ii) Prostatic Cancer Cells

Figure 3:
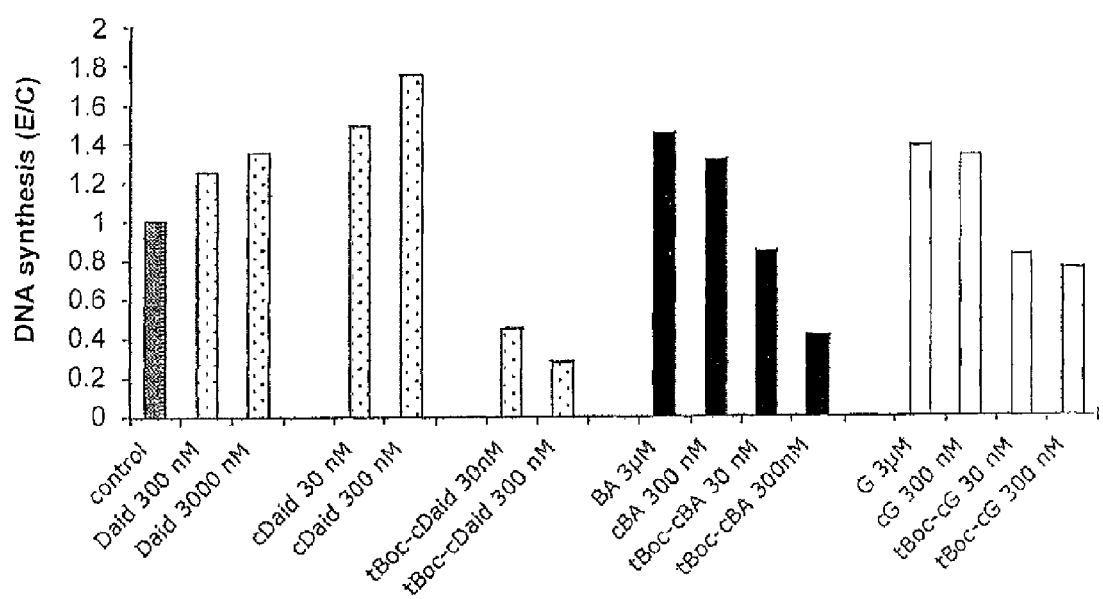
FIG. 3 is a graph showing the effect of isoflavone derivatives on DNA synthesis in human prostate C4-2B cancer cells assessed by [$^3$H]-thymidine incorporation. Results are expressed as the ratio between [$^3$H]-thymidine incorporation in isoflavone treated versus control cells (E/C). BA=compound 1; cBA=compound 4; t-BoccBA=compound 7; G=compound 2; cG=compound 5; t-BoccG=compound 8; Daid=compound 3; cDaid=compound 6; t-Boc-cDaid=compound 9.

C4-2B cells. In these cells, the underivatized isoflavone genistein 2, stimulated DNA synthesis significantly at 3 μM, and its respective carboxy alkyl derivative 5 stimulated DNA synthesis at 300 nM. The t-Boc derivative 8 at 30 nM and 300 nM, slightly inhibited DNA synthesis by 10-15%, as shown in FIG. 3.

(iii) Adrenocarcinoma Cells

H295R cells. The t-Boc derivative 8 at 3 μM inhibited 40 to 45% DNA synthesis.

(iv) Mammary Cancer Cells

T47D mammary cancer cells. Compound 8 at 10 μM inhibited DNA synthesis moderately by 24 to 40%.

Figure 1C:
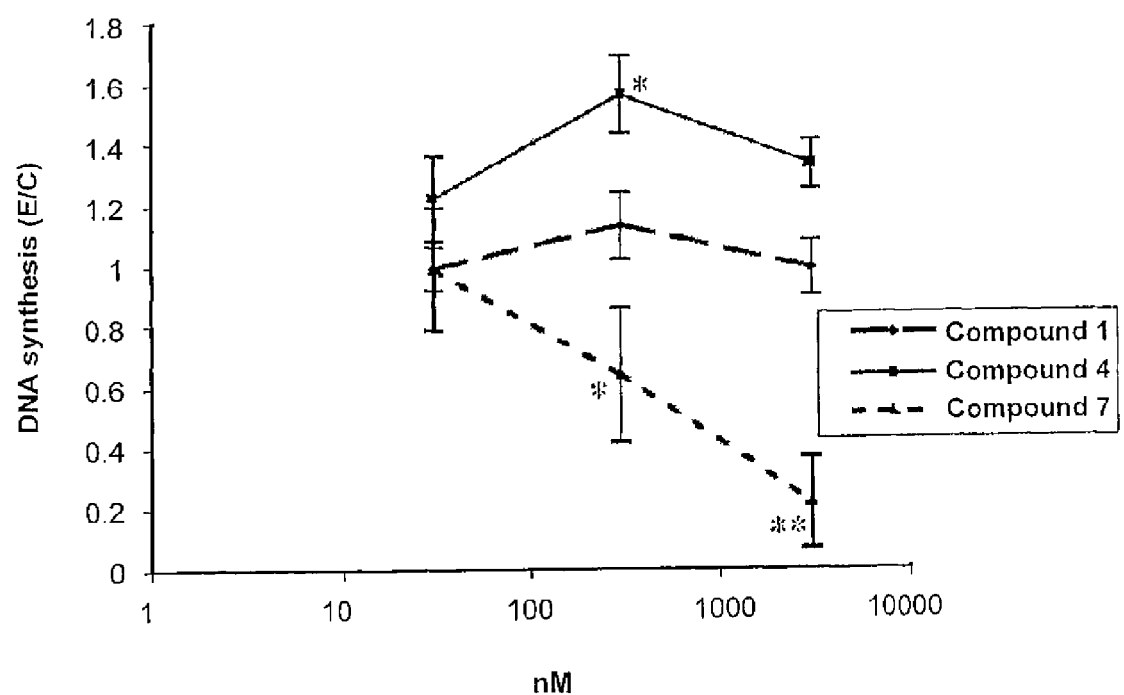

Biochanin A and its Derivatives (Compounds 1, 4 and 7)
(i) Cancerous Cells of the Gastrointestinal Tract (a) 320DM colon cancer cells. Compound 1 (30 to 3000 nM) had no effect on growth, as shown in FIGS. 1A and 1C. Its 2-carboxypropylene derivative 4 (30 to 3000 nM), stimulated the DNA synthesis, while the t-Boc derivative 7 (30 to 3000 nM) inhibited significantly DNA synthesis in these cells.

(b) N87 gastric carcinoma cells. Compound 4 at 300 nM stimulated DNA synthesis by 50% whereas the t-Boc derivative 7 (300 nM) inhibited cell growth by 40%. Compound 1 at 3 μM had no effect in N87 cells (data not shown).

(ii) Prostatic Cancer Cells

C4-2B cells. In these cells, the underivatized isoflavone biochain A (1), stimulated DNA synthesis significantly at 3 μM, and its carboxyalkylene derivative 4, stimulated DNA

TABLE 2

Inhibition of DNA synthesis$^a$ by compounds 7, 8, 9 and estrogen

| Compound | 320DM | MLS | Cells A2780 | H295R | C4-2B | VSMC |
|---|---|---|---|---|---|---|
| 7 | 0.22 ± 0.15 | 0.05 ± 0.23 | 0.64 ± 0.16 | 0.55 ± 0.03 | 0.41 ± 0.27 | 0.74 ± 0.05 |
| 8 | 0.2 ± 0.09 | N.D. | 1.12 ± 0.19 | 0.6 ± 0.14 | 0.75 ± 0.07 | 0.78 ± 0.1 |
| 9 | 0.08 ± 0.01 | 0.03 ± 0.07 | 0.1 ± 0.15 | 0.08 ± 0.21 | 0.28 ± 0.2 | 0.73 ± 0.13 |
| E2 | 1.64 ± 0.13 | 1.39 ± 0.03 | 1.42 ± 0.10 | 2.10 + .10 | 2.10 ± 0.10 | 0.55 ± 0.12 |

$^a$Compounds 7, 8 and 9 were used at 0.3 μM in the prostatic cell line C4-2B and at 3 μM in all the other cells;
E2 was used at 30 nM throughout;
N.D.: not determined Example 5

In Vitro Effect of Isoflavones, Carboxyalkylene and T-Boc Derivatives Thereof on DNA Synthesis The effect of biochain A (compound 1), genistein (compound 2) and daidzein (compound 3) and their carboxyalkylene and t-Boc derivatives (compounds 4-9) on DNA synthesis in various cancer cell lines was assessed by [$^3$H]-thymidine incorporation, as described in Materials and Methods above.

The inhibitory effect of the derivatives 7-9 of the invention was also compared to the inhibitory effect of the ER inhibitor ICI 182780 and assessed in the presence of estradiol and of known apoptosis inhibitors such as Z-VAD-FMK.

synthesis at 300 nM. The t-Boc derivative 7 at 30 nM inhibited DNA synthesis only by 10%, but 300 nM of 7 inhibited synthesis by 50%. The results are shown in FIG. 3.

(iii) Adrenocarcinoma Cells

H295R cells. Compound 4 stimulated DNA synthesis by 273%, while the parent compound 1 (3 μM) had no effect on DNA synthesis. On the other hand, the t-Boc derivatives 7 at 3 μM inhibited 40 to 45% DNA synthesis, as compared to daunomycin at 3 μM, which inhibited the growth of these cells by 75% under the same experimental conditions (data not shown).

(iv) Mammary Cancer Cells

T47D mammary cancer cells. Compound 1 at 10 μM stimulated DNA synthesis, while the carboxypropylene derivative 4 had no effect.

(v) Normal Human Vascular Smooth Muscle Cells

Compound 1 and the corresponding carboxyalkylene derivative and 4 stimulated DNA synthesis at 300 nM, while the t-Boc derivative 7 (3.3 µM) inhibited DNA synthesis only moderately (by 26%), (data not shown).

Daidzein and its Derivatives (Compounds 3, 6 and 9)

(i) Cancerous Cells of the Gastrointestinal Tract

320DM Colon Cancer Cells

Figure 2A:
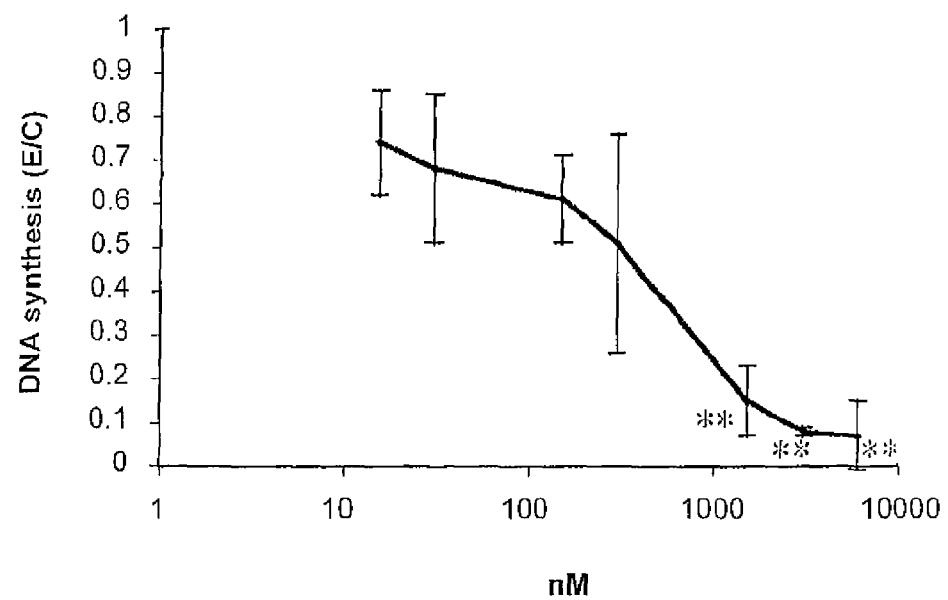
FIGS. 2A-2B are graphs showing the effect of varying concentrations of compound 9 on DNA synthesis in 320DM human colon (2A) and MLS ovarian (2B) cancer cells assessed by [$^3$H]-thymidine incorporation. Results, calculated as means±SD of 8-16 incubates from 2-4 experiments, are expressed as the ratio between [$^3$H]-thymidine incorporation in isoflavone treated versus control cells (E/C).

As shown in FIG. 2A, compound 9 (15 to 6000 nM) induced dose dependent decreases in [$^3$H]-thymidine incorporation into DNA in 320DM human colon cancer cells. A plateau of inhibition of DNA synthesis was reached after 72 h of incubation. In these cells, a concentration of 3 µM of compounds 3 and 6 increased DNA synthesis by 155 to 259% (data not shown).

[$^3$H]-thymidine incorporation was significantly increased (206%, p<0.01) when the 320DM cells were exposed to 30 nM estradiol. The stimulatory DNA synthesis by estradiol in these cells was suppressed to basal levels (100%) in the presence of 0.3 µM compound 9, or to 63% in the presence of 1.1 µM ICI 182780, which is considered an "absolute" ER inhibitor. At 10 fold higher concentration of estradiol (300 nM), the DNA synthesis in these cells was similarly increased (p<0.01), but at this concentration of estradiol, compound 9 (0.3 µM) could not suppress its proliferative effect nor could 1.1 µM ICI 182780 (92% DNA synthesis). The results, expressed as the ratio between experimental and control (E/C) DNA synthesis are shown in Table 3. Results were calculated as means±SD of 8-16 incubates from 2-4 experiments.

The modulation of DNA synthesis by compound 9 in the presence of the general apoptosis inhibitor Z-VAD-FMK Me ester (Z-VADFK) was assessed by [$^3$H]-thymidine incorporation into DNA of 320DM colon cancer cells. The general apoptosis inhibitor at 25 µM had no effect on DNA synthesis in these cells, whereas 9 at 0.3 µM, inhibited DNA synthesis by 32%. However, when the cells were exposed to 9 (0.3 µM) in the presence of the general apoptosis inhibitor, the antiproliferative effect of 9 was not discernible. On the other hand, when the DNA synthesis in these cells was inhibited up to 96% by 3 µM of 9, 25 µM of the general apoptosis inhibitor was capable of recovering the DNA synthesis only up to 50%. The results, expressed as the ratio between experimental and control (E/C) DNA synthesis are shown in Table 4. Results were calculated as means±SD of 8-16 incubates from 2-4 experiments.

(ii) Ovarian Cancer Cells (a) MLS Ovarian Cells

Figure 2B:
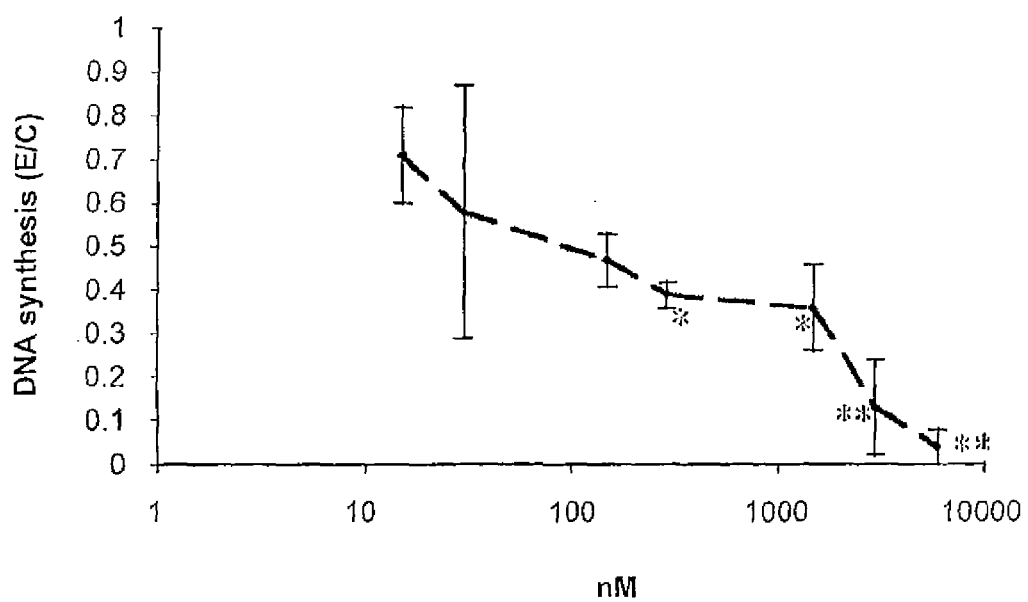

As shown in FIG. 2B, compound 9 (15 to 6000 nmol/l) induced dose dependent decreases in [$^3$H]-thymidine incorporation into DNA in ovarian MLS cells. A plateau of inhibition of DNA synthesis was reached after 72 h of incubation. In these cells, as well as in 320DM colon cells, concentration of 3 µM of compounds 3 and 6 increased DNA synthesis by 155 to 260% (data not shown).

The stimulatory DNA synthesis by estradiol (30 nM) in these cells (235%) was suppressed to basal levels (96%) in the presence of 0.3 µM, compound 9, or to 53% in the presence of 1.1 µM ICI 182780. At concentration of 0.3 µM estradiol, the DNA synthesis in these cells was increased to 187% (p<0.01), and compound 9 (0.3 µM) given simultaneously, could not suppress its proliferative effect nor could 1.1 µM ICI 182780 (95% DNA synthesis). The results, expressed as the ratio between experimental and control (E/C) DNA synthesis are shown in Table 3.

The modulation of DNA synthesis by compound 9 was assessed in the presence of the general apoptosis inhibitor Z-VADFK. At 25 µM, the general apoptosis inhibitor had no effect on DNA synthesis in these cells. Compound 9 at 0.3 µM given alone, inhibited DNA synthesis by 26%, but when given together with 25 µM Z-VADFK, was not capable of decreasing proliferation (DNA synthesis remained as high as 132%). On the other hand, when the DNA synthesis in these cells was inhibited 56% by 3 µM of 9, the general apoptosis inhibitor (25 µM) was capable of reversing the inhibitory effect of 9 on DNA synthesis. The results are shown in Table 4.

TABLE 3

Inhibitory effect of compound 9 and ICI 182780 on DNA synthesis in the presence of estradiol (E2)

| | Cells | |
|---|---|---|
| Compound | MLS | 320DM |
| None (control) | 1 ± 0.15 | 1 ± 0.12 |
| E2 (30 nM) | 2.35 ± 0.06** | 2.06 ± 0.09** |
| E2 (0.3 µM) | 1.70 ± 0.15* | 1.87 ± 0.18** |
| 9 (0.3 µM) | 0.61 ± 0.10* | 0.63 ± 0.11** |
| 9 + E2 (30 nM) | 0.96 ± 0.24 | 1.08 ± 0.16 |
| 9 + E2 (0.3 µM) | 2.39 ± 0.07 | 1.90 ± 0.05 |
| ICI 182780 (1.1 µM) | 0.52 ± 0.12** | 0.63 ± 0.08** |
| ICI 182780 + E2 (30 nM) | 0.53 ± 0.11 | 0.63 ± 0.08** |
| ICI 182780 + E2 (0.3 µM) | 0.95 ± 0.08 | 0.92 ± 0.18 |

*p < 0.05;
**p < 0.01

TABLE 4

Modulation of the inhibitory effect of compound 9 on DNA synthesis by the general apoptosis inhibitor Z-VADFK

| | Cells | |
|---|---|---|
| Treatment | MLS | 320DM |
| Control | 1 ± 0.07 | 1 ± 0.16 |
| Z-VADFK (25 µM) | 1.06 ± 0.1 | 1.11 ± 0.08 |
| 9 (0.3 µM) | 0.74 ± 0.11* | 0.68 ± 0.14* |
| 9 (0.3 µM) + Z-VADFK | 1.32 ± 0.26 | 1.18 ± 0.14 |
| 9 (3 µM) | 0.44 ± 0.14** | 0.04 ± 0.22** |
| 9 (3 µM) + Z-VADFK | 0.76 ± 0.16 | 0.5 ± 0.11* |

*p < 0.05;
**<0.01

(b) A2780 Cells

Compound 9 at concentrations ranging from 0.3 to 10 µM inhibited DNA synthesis by 60 to 90%. Under the same experimental conditions carboplatin, the cytotoxic drug used for the treatment of ovarian carcinoma, at a concentration of 3 µM, inhibited DNA synthesis in A2780 cells only by 57%. Interestingly, compound 8 (3 µM) had no effect in these cells, and 7 (3 µM) inhibited moderately (35%) their growth. Higher concentrations of the parent compounds (25 µM) 2 and 3 were needed to inhibit cell proliferation in these cells by 30 to 40%.

(iii) Prostatic Cancer Cells

C4-2B cells. The underivatized isoflavone daidzein (3), stimulated DNA synthesis significantly at 3 µM, and its respective carboxyalkylne derivative 6 stimulated DNA synthesis at 300 nM. On the other hand, the t-Boc derivative 9 at 30 nM and 300 nM, inhibited DNA synthesis by 30 and ~50%, respectively (FIG. 3).

(iv) Adrenocarcinoma Cells

H295R cells. Compound 9 was the most potent DNA synthesis inhibitor at 3 µM, inhibiting growth by 92%. Under the same experimental conditions, daunomycin at 3 µM inhibited the growth of these cells by 75% (data not shown).

(v) Mammary Cancer Cells

T47D mammary cancer cells. Compound 3 and its carboxymethylene derivative 6, at 10 μM, stimulated DNA synthesis, while the t-Boc derivatives 9 at 10 μM inhibited DNA synthesis moderately by 24 to 40%.

(vi) Normal Human Vascular Smooth Muscle Cells

Compound 3 and the corresponding carboxyalkylene derivative 6 stimulated DNA synthesis at 300 nM (data not shown).

Example 6

In Vitro Screening for Cytotoxicity of Compound 9 in Various Cancer Cell Lines 60 different cell lines were screened for the cytotoxicity of compound 9 using the In Vitro Cell Line Screening Project (IVCLSP), a service provided by the National Cancer Institute (NCI) of the US, as described in Material and Methods.

Figure 4:
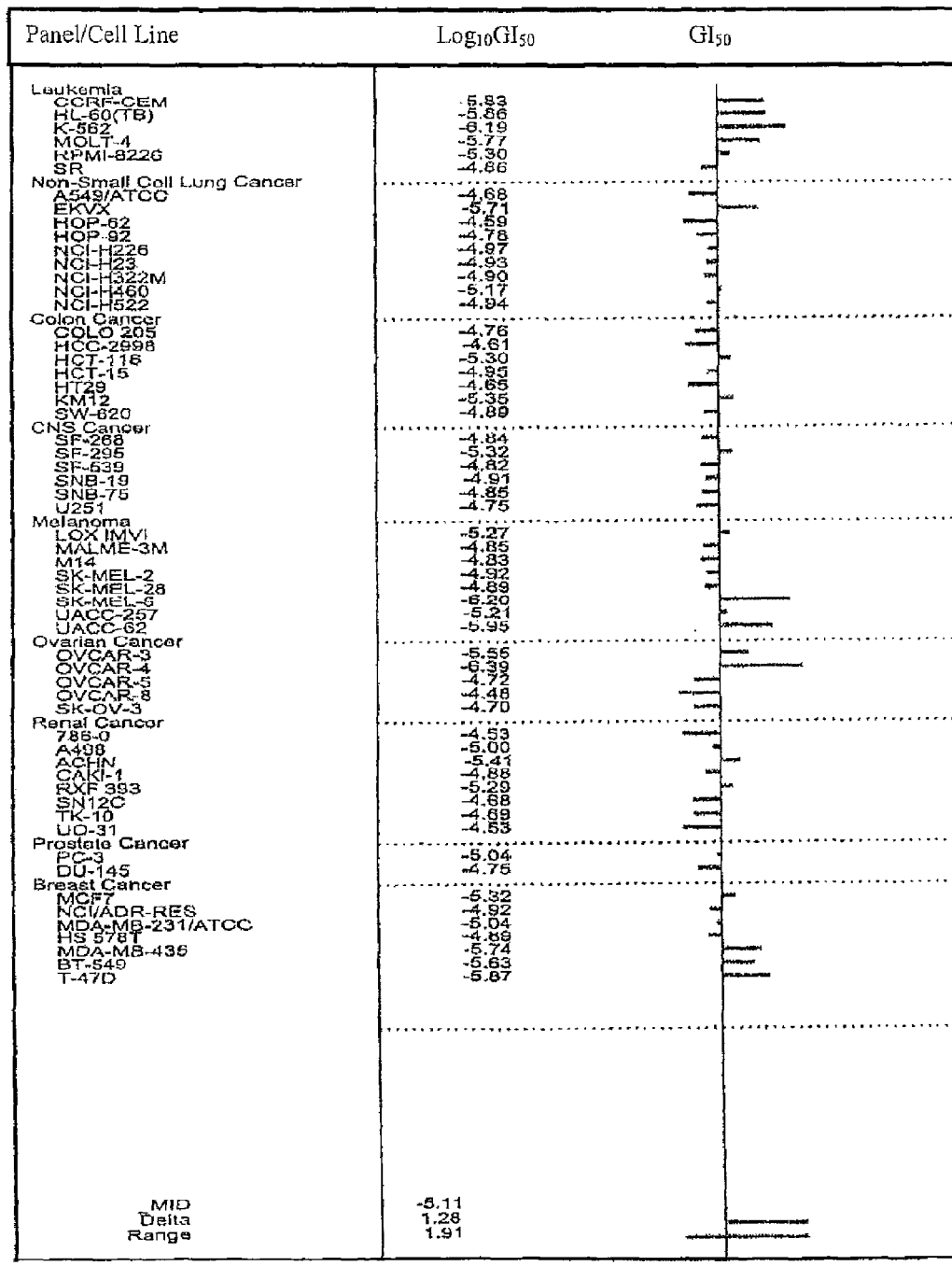
FIG. 4 shows a mean graph of GI$_{50}$ values and Log$_{10}$GI$_{50}$ values obtained for compound 9 tested on 60 cell lines. The midline of the graph represents the mean of the GI$_{50}$ endpoints calculated across all 60 cell lines. Subtraction of the mean value from the value for each individual cell line is presented as a horizontal bar. Cells line more sensitive to 9 are visualized as bars deflected to the right, while more resistant cell lines present bars extending to the left of the mean.
Figure 6:
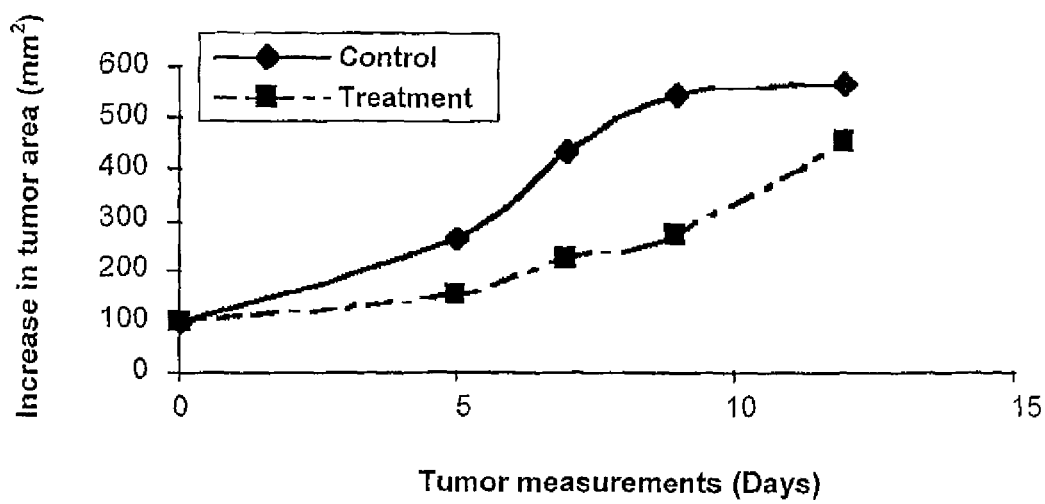
FIG. 6 is a graph showing the effect of compound 8 on the growth of 320DM colon xenografts implanted in nude mice. Control: mice injected with propylene glycol:PBS (5 mice); treatment: mice injected with compound 8 dissolved in propylene glycol:PBS (8 mice). The increase in tumor area on each day of tumor measurement is expressed as the ratio of the mean tumor area (control or treated mice) versus tumor area on Day 0 (control or treated mice, taken as 100%).

A graphical presentation (mean graph) of $GI_{50}$ (the negative $\log_{10}$ values of the concentration required to inhibit the growth of a cell line by 50% relative to untreated cells; see Materials and Methods) is shown in FIG. 4. As shown in FIG. 6 and summarized in Table 5, the cell lines which were more sensitive to the cytotoxic effect of 9 were the leukemia cell lines, particularly K-562, breast cancer cell lines, particularly MDA-MB-435 and T-47D, melanoma cell lines, particularly SK-MEL-5, the ovarian cancer cell line OVCAR-4 and the non small lung cancer cell line EKVX.

TABLE 5

Cytotoxicity of compound 9 in highly sensitive human tumor cell lines

| Cell line | $\log_{10} GI_{50}$ |
|---|---|
| Leukemia | |
| K-562 | −6.19 |
| Breast cancer | |
| MDA-MB-435 | −5.74 |
| T-47D | −5.87 |
| Melanoma | |
| SK-MEL-5 | −6.20 |
| Ovarian cancer | |
| OVCAR-4 | −6.39 |
| Non small lung cancer | |
| EKVX | −5.71 |

Example 7

In Vivo Effect of Compound 9 in Mice Bearing MLS Xenografts

Figure 5:
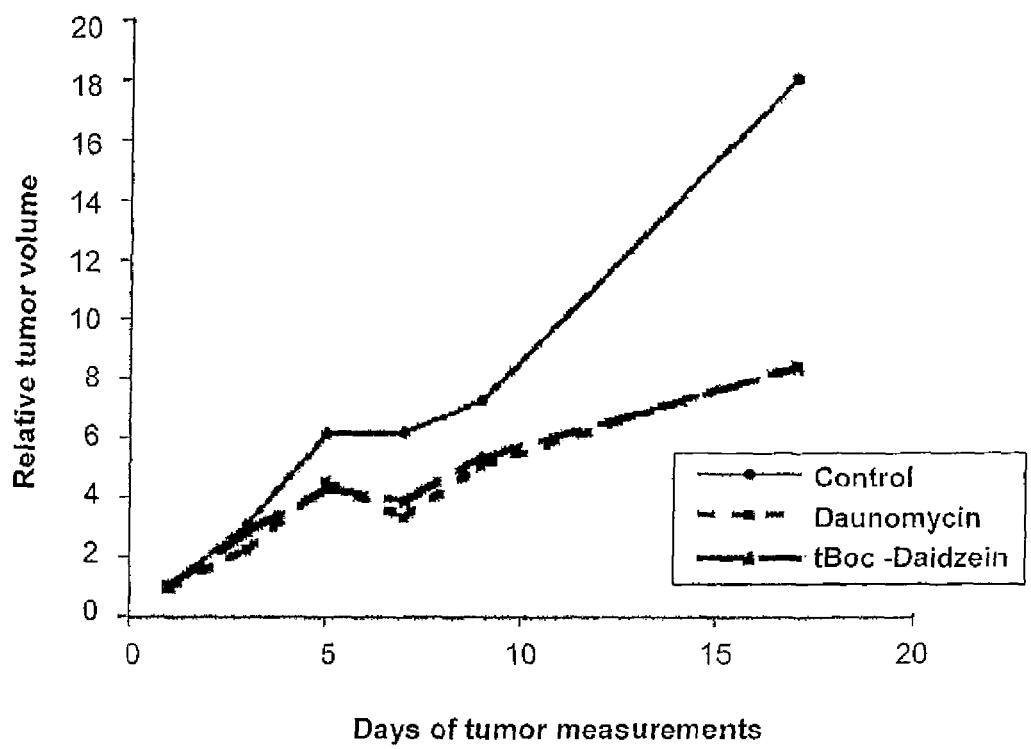
FIG. 5 is a graph showing the growth inhibitory effect of compound 9 on MLS ovarian xenografts implanted in nude mice (30 females). Relative tumor volume (y-axis) is calculated as the average tumor volume on day of tumor measurement relative to day 1.

Thirty female nude mice (8 weeks old) were inoculated sub-cutaneously (sc) with MLS ovarian carcinoma cells (1.5× $10^6$/mouse). Ten days later, when the tumors were palpable, the mice were randomly divided into 3 groups (8-10 mice/group). The mice in each group were iv injected every other day either with a vehicle (Neowater, a solubilization enhancer, 0.1 ml), daunomycin dissolved in Neowater (200 μg/mouse in 0.1 ml vehicle, total dose during treatment 1 mg/mouse), or compound 9 dissolved in Neowater (400 μg/mouse in 0.1 ml vehicle, total dose during treatment 2 mg/mouse). During treatment, body weight was recorded to monitor toxicity of the treatment, and the tumors were measured with an external caliper. Tumor volume was calculated using the formula length×width×height×π/6. Statistical significance was assessed using student's t test, and differences were considered significant at p<0.05. The average growth curve of the tumors in each group is shown in FIG. 5.

Tumor growth in the groups treated with 9 and daunomycin were inhibited by >50% as compared to the tumors of untreated mice. No weight reduction or death was seen in mice treated with 9, whereas daunomycin alone induced 15% reduction in mean body weight and caused death of 2 mice.

Example 8

In Vivo Effect of Compound 8 in Mice Bearing 320DM Xenografts

Thirty female CD-1 nude mice were inoculated sc with $2\times10^6$ 320DM human colon cancer cells. Two weeks later, 13 mice that developed palpable tumors were divided into two groups: control (5 mice) and treatment (8 mice). Each mouse of the treatment group received daily intra-peritoneal (ip) injections of compound 8 (230 μg in 70 μl of propylene glycol:PBS (20:80)) and the control mice received only propylene glycol:PBS. Each treated mouse received 9 injections within 11 days. The tumors were measured with calipers every other day during 12 days in two dimensions, length (a) and width (b), and tumor area was calculated using the formula: $r^2\times3.14$, where r=a/2+b/2/2. The tumor area on Day 0 was taken as 100%.

The effect of compound 8 on the growth of 320DM colon xenografts is shown in FIG. 6. The treatment slowed down the growth of the tumors, and the growth inhibitory effect of 8 was significant between day 0 and day 5 (p<0.037).

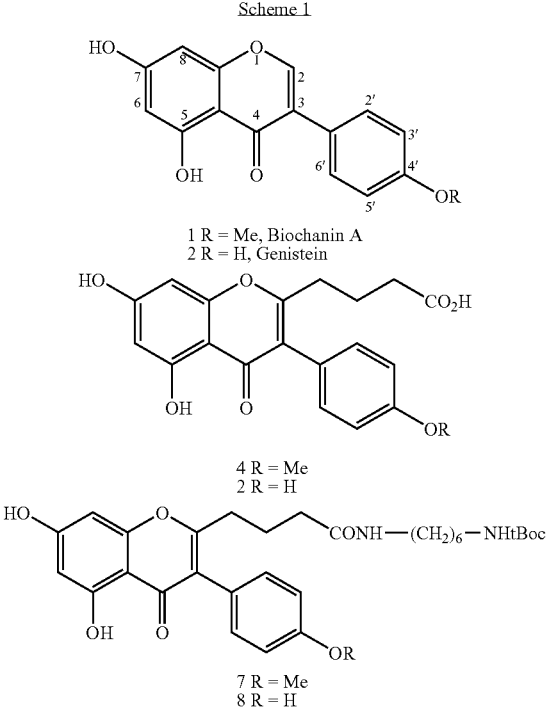

Scheme 1

1 R = Me, Biochanin A
2 R = H, Genistein

4 R = Me
2 R = H

7 R = Me
8 R = H

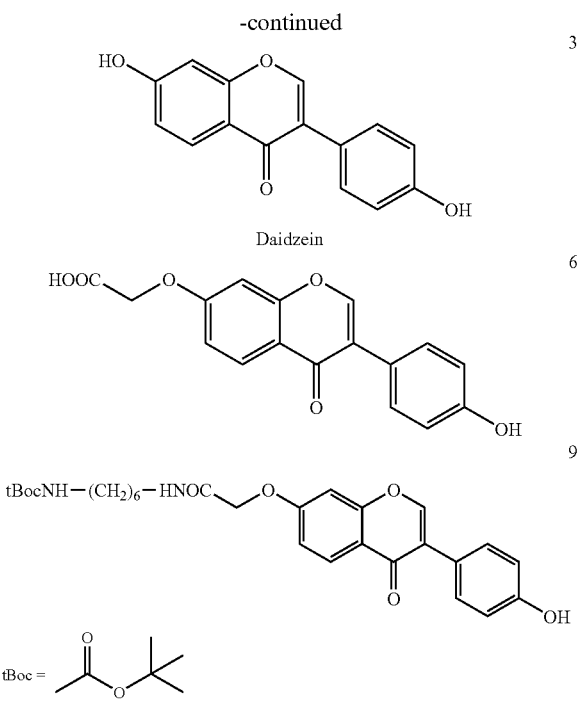

REFERENCES

Akiyama T., Ishida J., Nakagawa S., Ogawara H., Watanabe S. et al., (1987) "Genistein, a specific inhibitor of tyrosine-specific protein kinases". *J Bioi Chem,* 262:5592-5595.

Agarwal R. (2000), "Cell signaling and regulators of cell cycle as molecular targets for prostate cancer prevention by dietary agents". *Biochem. Pharmaco.,* 60: 1051-1059.

Barve V., Ahmed F., Adsule S., Banerjee S., Kulkarni S. et al. (2006) "Synthesis, molecular characterization and biological activity of novel synthetic derivatives of chromen-4-one in human cancer cells". *J Med Chem,* 49:3800-3808.

Bennetau-Pelissero, C., Le Houerou, C., Lamothe, V., Le Menn F., Babin, P., Bennetau, B., (2000), "Synthesis of Haptens and Conjugates for ELISAs of Phytoestrogens", Development of the Immunological Tests, *J. Agric. Food Chem.,* 48:305-311.

Gamble J. R., Xia P., Hahn C. N., Drew J. J., Drogemuller C. J. et al. (2006), "Phenoxodiol, an experimental anticancer drug, shows potent antiangiogenic properties in addition to its antitumour effects". *Int J Cancer,* 118:2412-2420.

Harris D., M., Besselink E., Henning S. M., Go V. L. and Heber D., (2005), "Phytoestrogens induce differential estrogen receptor alpha- or beta-mediated responses in transfected breast cancer cells". *Exp Bioi Med (Maywood),* 230:558-568.

Kamsteeg M., Rutherford T., Sapi E., Hanczarul B., Sharabi S., Flick M., Brown D. and Mor G., (2003), "Phenoxodiol—an isoflavone analog—induces apaptosis in chemoresistant ovarian cancer cells". *Oncogene,* 22:2611-2620.

Kim H., Peterson T. G. and Barnes S. (1998), "Mechanisms of action of the soy isoflavone genistein: emerging role for its effects via transforming growth factor beta signaling pathways". *Am J. Clin. Nutr.,* 68:1418 S-1425S.

Kuiper G. G., Lemmen J. G., Carlsson B., Corton J. C., Safe, S. H. et al. (1998), "Interaction of estrogenic chemicals and phytoestrogens with estrogen receptor beta", *Endocrinology,* 139:4252-4263.

Mor G., Fu H. H. and Alvero A. B. (2006), "Phenoxodiol, a novel approach for the treatment of ovarian cancer". *Curr Opin Investig Drugs,* 7:542-548.

Pelter, A.; Ward, R.; Whalley, J. (1998), A facile synthesis of 2-substituted isoflavones for immunoassay: Assembly of the isoflavonoid skeleton by means of a novel cyclisation reaction. *Synthesis,* 1793-1802.

Sarkar F. H., Adsule S., Padhye S., Kulkarni S., Li Y. (2006), "The role of genistein and synthetic derivatives of isoflavone in cancer prevention and therapy". *Mini Rev Med Chem,* 6:401-407.

Somjen D., Kohen F., Jaffe A., Amir-Zaltsman Y., Knoll E. and Stern N. 1998), "Effects of gonadal steroids and their antagonists on DNA synthesis in human vascular cells", *Hypertension* 32:39-45.

Somjen D., Kohen F., Amir-Zaltsman Y., Knoll E., Stem N., (2000), Vitamin D analogs modulate the action of gonadal steroids in human vascular cells in vitro. *Am J Hypertens,* 13:396-403.

Somjen, D.; Amir-Zaltsman, Y.; Gayer, B.; Kulik, T.; Knoll, E.; Stern, N.; Lu, L. J.; Toldo, L.; Kohen, F. (2002), 6-Carboxymethyl genistein: a novel selective oestrogen receptor modulator (SERM) with unique, differential effects on the vasculature, bone and uterus. *J Endocrinol.* 173:415-427.

Uckun F. M., Narla R. K., Jun X., Zeren T., Venkatachalam T. et al. (1998), "Cytotoxic activity of epidermal growth factor-genistein against breast cancer cells". *Clin Cancer Res,* 4:901-912.

The invention claimed is:

1. An isoflavone derivative of formula I:

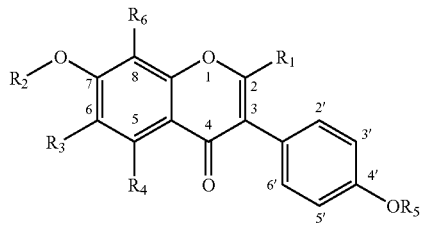

wherein $R_1$ is H or $R_7$—CON($R_8$)—$R_9$—N($R_8$)—B;
$R_2$ is H, ($C_1$-$C_6$) alkyl, $R_9$—COOR$_{10}$, glucosyl, or $R_7$—CON($R_8$)—$R_9$—N($R_8$)—B;
$R_3$ is H or $R_7$—COOR$_{10}$;
$R_4$ is H, OH, —OR$_9$-COR$_{10}$ or $R_7$—COOR$_{10}$;
$R_5$ is H, ($C_1$-$C_6$) alkyl or $R_7$—COOR$_{10}$
$R_6$ is H or $R_7$—COOR$_{10}$;
$R_7$ is ($C_1$-$C_{20}$) alkylene, —O—($C_1$-$C_{20}$) alkylene or ($C_2$-$C_{20}$) alkenylene;
$R_8$ is H or ($C_1$-$C_3$) alkyl;
$R_9$ is ($C_1$-$C_{20}$) alkylene or ($C_2$-$C_{20}$) alkenylene;
$R_{10}$ is H or $R_7$—CON($R_8$)—$R_9$—N($R_8$)—B;
B is an amino-protecting group;
provided that at least one of $R_1$ and $R_2$ is $R_7$—CON($R_8$)—$R_9$—N($R_8$)—B;
and a pharmaceutically acceptable salt or hydrate thereof.

2. The isoflavone derivative according to claim 1, wherein said amino protecting group B is selected from the group consisting of tert-butoxycarbonyl; benzyloxycarbonyl; 4-methoxybenzyloxycarbonyl; 2-nitrobenzyloxycarbonyl; 2-(biphenyl-4-yl)-2-propoxycarbonyl; and fluorenyl-9-methoxycarbonyl.

3. The isoflavone derivative according to claim 2, wherein said amino protecting group is tert-butoxycarbonyl.

4. An isoflavone derivative according to claim 1 of the formula Ia:

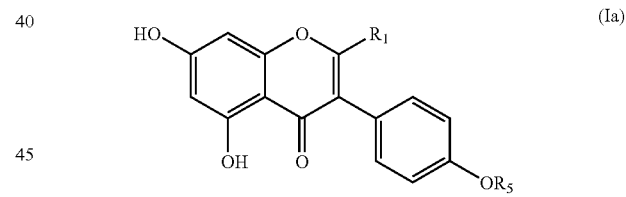

wherein $R_1$ is $R_7$—CON($R_8$)—$R_9$—N($R_8$)—B;
$R_5$ is H or ($C_1$-$C_6$) alkyl;
$R_7$ is ($C_1$-$C_{20}$) alkylene, —O—($C_1$-$C_{20}$) alkylene or ($C_2$-$C_{20}$) alkenylene;
$R_8$ is H or ($C_1$-$C_3$) alkyl;
$R_9$ is ($C_1$-$C_{20}$) alkylene or ($C_2$-$C_{20}$) alkenylene;
B is an amino-protecting group;
and a pharmaceutically acceptable salt or hydrate thereof.

5. The isoflavone derivative according to claim 4, wherein R5 is H or (C1-C3) alkyl, R7 is (C3-C6) alkylene, R8 is H or (C1-C3) alkyl, R9 is (C3-C8) alkylene and B is tert-butoxycarbonyl.

6. The isoflavone derivative according to claim 5, herein identified as compound 7, of the formula:

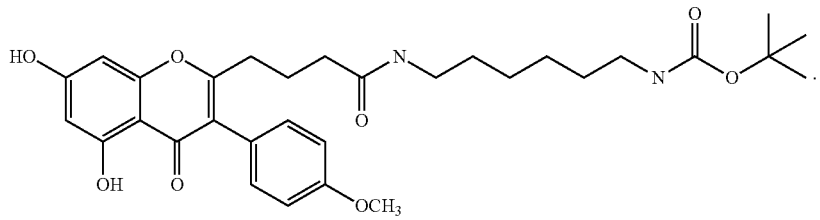

7. The isoflavone derivative according to claim 5, herein identified as compound 8, of the formula:

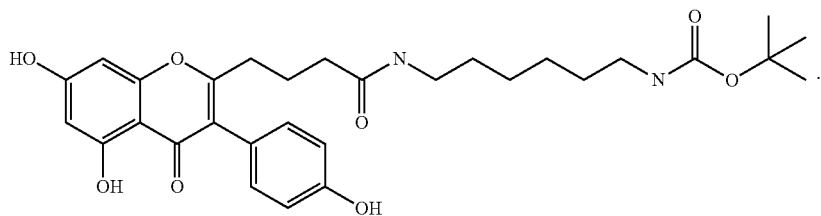

8. The isoflavone derivative according to claim 1 of the formula Ib:

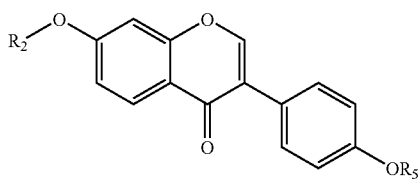

wherein
$R_2$ is $R_7$—CON($R_8$)—$R_9$—N($R_8$)—B;
$R_5$ is H or ($C_1$-$C_6$) alkyl
$R_7$ is ($C_1$-$C_{20}$) alkylene, —O—($C_1$-$C_{20}$) alkylene or ($C_2$-$C_{20}$) alkenylene;
$R_8$ is H or ($C_1$-$C_3$) alkyl;
$R_9$ is ($C_1$-$C_{20}$) alkylene or ($C_2$-$C_{20}$) alkenylene;
B is an amino-protecting group;
and a pharmaceutically acceptable salt or hydrate thereof.

9. The isoflavone derivative according to claim 8, wherein $R_5$ is H, $R_7$ is ($C_1$-$C_6$) alkylene, $R_8$ is H or ($C_1$-$C_3$) alkyl, $R_9$ is ($C_3$-$C_{10}$) alkylene and B is tert-butoxycarbonyl.

10. The isoflavone derivative according to claim 9, herein identified as compound 9, of the formula:

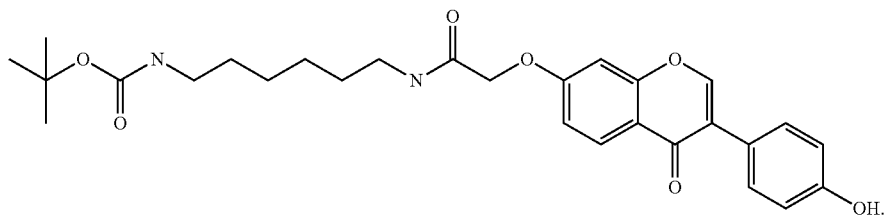

11. A pharmaceutical composition comprising an isoflavone derivative according to claim 1, or a pharmaceutically acceptable salt or hydrate thereof.

12. A pharmaceutical composition comprising an isoflavone derivative according to claim 6, or a pharmaceutically acceptable salt or hydrate thereof.

13. A pharmaceutical composition comprising an isoflavone derivative according to claim 7, or a pharmaceutically acceptable salt or hydrate thereof.

14. A pharmaceutical composition comprising an isoflavone derivative according to claim 10, or a pharmaceutically acceptable salt or hydrate thereof.

15. The pharmaceutical composition according to claim 11, for treating a disease associated with estrogen receptor functioning.

16. A method of treating a disease or disorder associated with estrogen receptor functioning, comprising administering to a subject in need thereof a therapeutically effective amount of an isoflavone derivative according to claim 1.

17. The method according to claim 16, wherein said disease or disorder associated with estrogen receptor functioning is selected from a cancer, bone loss, bone fractures, osteoporosis, metastatic bone disease, Paget's disease, periodontal disease, cartilage degeneration, endometriosis, uterine fibroid disease, hot flashes, cardiovascular diseases, impairment of cognitive functioning, age-related mild cognitive impairment, cerebral degenerative disorders, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, sleep disorders, irritability, impulsivity, multiple sclerosis, Parkinson's disease, inflammation, inflammatory bowel disease, irritable bowel syndrome, sexual dysfunction, hypertension or retinal degeneration.

18. The method according to claim 17, wherein said cancer is selected from breast cancer, uterus cancer, ovarian cancer, colon cancer, gastric cancer, adrenal cancer, leukemia, non small lung cancer, melanoma and prostate cancer.

19. The method according to claim 18, wherein said breast cancer is an estrogen-dependent cancer.

* * * * *